(12) United States Patent
Ballard et al.

(10) Patent No.: US 7,235,547 B2
(45) Date of Patent: Jun. 26, 2007

(54) PHARMACEUTICAL COMPOSITION COMPRISING AN ACHE INHIBITOR AND A MGLUR2 ANTAGONIST

(75) Inventors: Theresa Maria Ballard, Lutter (FR); Silvia Gatti McArthur, Basel (CH); Erwin Goetschi, Reinach (CH); Juergen Wichmann, Steinen (DE); Thomas Johannes Woltering, Weil am Rhein (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 347 days.

(21) Appl. No.: 10/896,494

(22) Filed: Jul. 22, 2004

(65) Prior Publication Data

US 2005/0049243 A1 Mar. 3, 2005

(30) Foreign Application Priority Data

Jul. 25, 2003 (EP) .................................. 03016968

(51) Int. Cl.
*A01N 43/62* (2006.01)
*A01N 43/40* (2006.01)
*A61K 31/5513* (2006.01)

(52) U.S. Cl. ........................ 514/221; 514/212; 514/215

(58) Field of Classification Search ................ 514/221, 514/212, 215
See application file for complete search history.

(56) References Cited

U.S. PATENT DOCUMENTS

| 4,663,318 | A | * | 5/1987 | Davis ........................... 514/215 |
| 4,895,841 | A | | 1/1990 | Sugimoto et al. |
| 5,100,901 | A | * | 3/1992 | Sugimoto et al. ........... 514/319 |
| 6,194,403 | B1 | | 2/2001 | Hu et al. |
| 6,500,954 | B1 | * | 12/2002 | Gouliaev et al. ........... 546/139 |
| 6,500,955 | B1 | * | 12/2002 | Chawla et al. .............. 546/168 |
| 6,500,972 | B2 | * | 12/2002 | Cheng et al. ................ 552/296 |
| 6,949,542 | B2 | * | 9/2005 | Adam et al. ................. 514/221 |
| 2002/0193367 | A1 | | 12/2002 | Adam et al. |
| 2002/0198197 | A1 | | 12/2002 | Adam et al. |
| 2003/0166639 | A1 | | 9/2003 | Adam et al. |

FOREIGN PATENT DOCUMENTS

EP 1 203 584 5/2000
WO WO 01/74339 A2 10/2001

OTHER PUBLICATIONS

2006 Chemical Abstracts Service Catalog, published by Chemical Abstracts Service, p. 52.*

Avery's Drug Treatment: Principles and Practice of Clinical Pharmacology and Therapeutics, 3rd Edition, 1987, Edited by Trevor M. Speight, Chapter VIII, pp. 255-282.*
Kano et al., J. Org. Chem. 48, pp. 3835-3837 (1983).
Bellamy et al., Tetrahedron Letters, 25, pp. 839-842 (1984).
Boyer et al., J. Heterocyclic Chem., 25, pp. 1003-1005 (1988).
Ishikawa et al., J. Med. Chem., 28, pp. 1387-1393 (1985).
Ohmori et al., J. Med. Chem., 37, 467-475 (1994).
Rathke et al., Synth. Commun., 15, pp. 1039-1049 (1985).
Fanta et al., Organic Synthesis, vol. 25, pp. 78-83 (John Wiley & Sons, Inc.) (1945).
Barnick et al., Synthesis, pp. 787-788 (1979).

* cited by examiner

*Primary Examiner*—Shaojia Anna Jiang
*Assistant Examiner*—Eric S. Olson
(74) *Attorney, Agent, or Firm*—George W. Johnston; Patricia S. Rocha-Tramaloni; Gene J. Yao

(57) ABSTRACT

The present invention relates to a pharmaceutical composition comprising an inhibitor of acetylcholinesterase (AChE inhibitor) and a metabotropic glutamate receptor 2 antagonist (mGluR2 antagonist) and a pharmaceutically acceptable excipient. The invention also relates to a method of treating and/or preventing acute and/or chronic neurological disorders comprising administering to a patient in need of such treatment and/or prevention a therapeutically effective amount of said AChE inhibitor and mGluR2 antagonist as well as a kit comprising said AChE inhibitor and mGluR2 antagonist. In particular, the mGluR2 antagonist relates to the compound of formula I

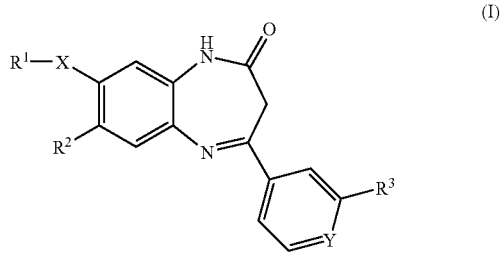

wherein, $R^1$, $R^2$, $R^3$, X and Y are described hereinabove. The combination of the AChE inhibitor and mGluR2 antagonist is useful for treating and/or preventing chronic neurological disorders. These disorders include Alzheimer's disease and mild cognitive impairment.

19 Claims, No Drawings

PHARMACEUTICAL COMPOSITION COMPRISING AN ACHE INHIBITOR AND A MGLUR2 ANTAGONIST

FIELD OF THE INVENTION

The present invention relates to a pharmaceutical composition comprising an inhibitor of acetylcholinesterase (AChE inhibitor) and a metabotropic glutamate receptor 2 antagonist (mGluR2 antagonist) and a pharmaceutically acceptable excipient. The invention also relates to a method of treating and/or preventing acute and/or chronic neurological disorders comprising administering to a patient in need of such treatment and/or prevention a therapeutically effective amount of said AChE inhibitor and mGluR2 antagonist as well as a kit comprising said AChE inhibitor and mGluR2 antagonist. In particular, the mGluR2 antagonist useful in compositions and methods of the invention have the formula I

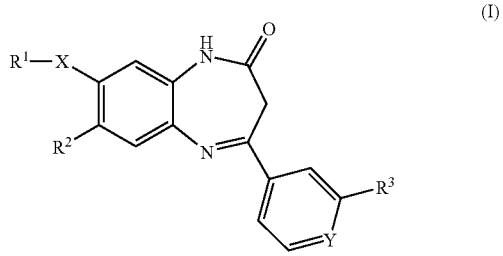

(I)

wherein, $R^1$, $R^2$, $R^3$, X and Y are described hereinbelow. The combination of the AChE inhibitor of the invention and mGluR2 antagonist is useful for treating and/or preventing chronic neurological disorders. These disorders include Alzheimer's disease. These disorders also include mild cognitive impairment.

BACKGROUND OF THE INVENTION

In the central nervous system (CNS) the transmission of stimuli takes place by the interaction of a neurotransmitter, which is sent out by a neuron, with a neuroreceptor. L-glutamic acid, the most commonly occurring neurotransmitter in the CNS, plays a critical role in a large number of physiological processes. The glutamate-dependent stimulus receptors are divided into two main groups. The first main group forms ligand-controlled ion channels. The metabotropic glutamate receptors (mGluR) form the second main group and, furthermore, belong to the family of G-protein-coupled receptors.

At present, eight different members of these mGluR are known and of these some even have sub-types. On the basis of structural parameters, the different influences on the synthesis of secondary metabolites and the different affinity to low-molecular weight chemical compounds, these eight receptors can be sub-divided into three sub-groups: mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the group II can be used for the treatment or prevention of acute and/or chronic neurological disorders such as psychosis, schizophrenia, Alzheimer's disease, cognitive disorders and memory deficits.

Other treatable indications in this connection are restricted brain function caused by bypass operations or transplants, poor blood supply to the brain, spinal cord injuries, head injuries, hypoxia caused by pregnancy, cardiac arrest and hypoglycemia. Further treatable indications are chronic and acute pain, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia and depressions.

SUMMARY OF THE INVENTION

An aspect of the present invention relates to a pharmaceutical composition comprising an inhibitor of acetylcholinesterase (ACHE inhibitor) and a metabotropic glutamate receptor 2 antagonist (mGluR2 antagonist) and a pharmaceutically acceptable excipient. Another aspect of this invention is a method of treating and/or preventing acute and/or chronic neurological disorders comprising administering to a patient in need of such treatment and/or prevention an effective amount of said AChE inhibitor and a mGluR2 antagonist. Yet another method aspect of this invention is a kit comprising said AChE inhibitor and a mGluR2 antagonist.

In particular, the mGluR2 antagonist relates to the compound of formula I

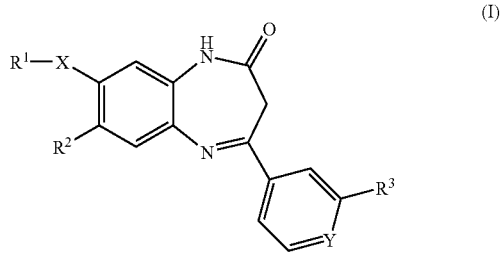

(I)

wherein,

X is a single bond or an ethynediyl group;

Y is —CH= or =N—;

$R^1$ is, in case X is a single bond, selected from hydrogen, cyano, halogen, $(C_1-C_7)$-alkyl, $(C_1-C_7)$-alkoxy, fluoro-$(C_1-C_7)$-alkyl, fluoro-$(C_1-C_7)$-alkoxy, pyrrol-1-yl, unsubstituted phenyl, and phenyl substituted by one or two substituents selected from the group consisting of halogen, $(C_1-C_7)$-alkyl and fluoro-$(C_1-C_7)$-alkyl; or $R^1$ is, in case X is an ethynediyl group, selected from unsubstituted phenyl, and phenyl substituted by one or two substituents selected from the group consisting of halogen, $(C_1-C_7)$-alkyl and fluoro-$(C_1-C_7)$-alkyl;

$R^2$ is selected from hydrogen, $(C_1-C_7)$-alkyl, $(C_2-C_7)$-alkenyl, $(C_1-C_7)$-alkoxy, halogen, —NR'R", pyrrolidin-1-yl, piperidin-1-yl, morpholine-4-yl, fluoro-$(C_1-C_7)$-alkyl, fluoro-$(C_1-C_7)$-alkoxy, and $(C_1-C_7)$-alkoxy-(ethoxy)$_m$; wherein m is 1, 2, 3 or 4; R' and R" are each, independently selected from hydrogen, $(C_1-C_7)$-alkyl and $(C_3-C_7)$-cycloalkyl; and $R^3$ is a six-membered aromatic heterocycle ring containing 1 to 3 nitrogen atoms or a pyridine-N-oxide, which ring is unsubstituted or substituted by one or two substituents selected from the group consisting of halogen, fluoro-$(C_1-C_7)$-alkyl, fluoro-$(C_1-C_7)$-alkoxy, cyano, amino, $(C_1-C_7)$-alkylamino, $(C_1-C_7)$-dialkylamino, $(C_1-C_7)$-alkoxy-$(C_1-C_7)$-alkylamino, $(C_1-C_7)$-hydroxy-$(C_1-C_7)$-alkylamino, —$(CH_2)_n$—C(O)—OR", —$(CH_2)_n$—C(O)—NR'R", —$(CH_2)_n$—SO$_2$—NR'R", —$(CH_2)_n$—C(NH$_2$)=NR", hydroxy, $(C_1-C_7)$-alkoxy, $(C_1-C_7)$-alkylthio, $C_3$–$C_7$-cycloalkyl, $(C_1-C_7)$-alkyl, and $(C_1-C_7)$-alkyl substituted by a group consisting of fluoro, —NR'R", hydroxy, $(C_1-C_7)$-alkoxy, pyrrolidin-1-yl, azetidin-1-yl, cyano and carbamoyloxy, wherein n is 0, 1, 2, 3 or 4; and R' and R" have the meanings specified above; or a pharmaceutically acceptable addition salt thereof.

DETAILED DESCRIPTION OF THE INVENTION

Non-limiting examples of AChE inhibitors include donepezil (Aricept), rivastigmine (Exelon), metrifonate (Promem), galantamine (Reminyl), physostigmine, tacrine (Cognex), fordine (Huperzine A), phenserine, citicoline (Neurox) and ganstigmine.

In a preferred embodiment, the AChE inhibitor is donepezil (Aricept) or a prodrug thereof, or a pharmaceutically acceptable salt or solvate of said compound or prodrug.

The AChE inhibitor and the mGluR2 antagonist may be administered separately, sequentially or simultaneously. Where the AChE inhibitor and the mGluR2 antagonist are administered simultaneously, they may be administered either in the same composition or in different compositions.

Acute and/or chronic neurological disorders include psychosis, schizophrenia, Alzheimer's disease, cognitive disorders and memory deficits like mild cognitive impairment, age-related cognitive decline, vascular dementia, Parkinsons's disease, memory impairment associated with depression or anxiety, Down's syndrome, stroke, traumatic brain injury, and attention deficit disorder. Other treatable indications are restricted brain function caused by bypass operations or transplants, poor blood supply to the brain, spinal cord injuries, head injuries, hypoxia caused by pregnancy, cardiac arrest and hypoglycemia. Further treatable indications are acute and chronic pain, Huntington's chorea, ALS, dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, nicotine addiction, psychotic episodes, opiate addiction, anxiety, vomiting, dyskinesia and depression.

In a preferred embodiment, the acute and/or chronic neurological disorder is Alzheimer's disease. In another preferred embodiment, the acute and/or chronic neurological disorder is mild cognitive impairment.

As used herein, a mammal in need of treatment of an acute and/or chronic neurological disorder means a mammal, and preferably a human, that is suffering from, or is at risk of suffering from, an acute and/or chronic neurological disorder.

As used herein, the terms "treat", "treating" and "treatment", and the like, as applied to an acute and/or chronic neurological disorder, refer to methods that slow, ameliorate, reduce or reverse such a disorder or any symptoms associated with said disorder, as currently afflicting the subject, as well as methods that prevent such a disorder or any symptoms thereof, from occurring.

The present invention further provides the use of an AChE inhibitor and a mGluR2 antagonist in the manufacture of a pharmaceutical composition (medicament) for treating an acute and/or chronic neurological disorder. The mGluR2 antagonist and an AChE inhibitor may be combined in a single medicament or maintained in separate medicaments.

In another embodiment the present invention provides a composition comprising an AChE inhibitor and a mGluR2 antagonist, e.g. a dihydro-benzo[b][1,4]diazepin-2-one derivative. In still another embodiment the present invention provides a composition comprising an AChE inhibitor and a compound of formula I as defined above.

The compounds of formula I can also be used in form of their prodrugs. Examples are esters, N-oxides, phosphate esters, glycoamide esters, glyceride conjugates and the like. The prodrugs may add to the value of the active compounds advantages in absorption, pharmacokinetics in distribution and transport to the brain.

All tautomeric forms of the compounds of formula I are also embraced herewith.

Unless otherwise stated, the following terms used in the present description have the definitions given in the following.

The term "ethynediyl group" denotes a group that contains a triple bond between two carbon atoms.

The term "$(C_1-C_7)$-alkyl" denotes straight-chain or branched saturated hydrocarbon residues with 1 to 7 carbon atoms, preferably with 1 to 4 carbon atoms, such as methyl, ethyl, n-propyl, i-propyl and the like.

The term "$(C_2-C_7)$-alkenyl" denotes straight-chain or branched unsaturated hydrocarbon residues with 2 to 7 carbon atoms, preferably with 2 to 4 carbon atoms, such as ethenyl or propenyl.

The term "$(C_1-C_7)$-alkoxy" denotes a $(C_1-C_7)$-alkyl residue in the sense of the foregoing definition bound via an oxygen atom. Examples of "$(C_1-C_7)$-alkoxy" residues include methoxy, ethoxy, isopropoxy and the like.

The term "halogen" embraces fluorine, chlorine, bromine and iodine.

The term "fluoro-$(C_1-C_7)$-alkyl" means a $(C_1-C_7)$-alkyl residue, wherein one or more hydrogen atoms are replaced by fluorine, for example trifluoromethyl. Accordingly, the term "fluoro-$(C_1-C_7)$-alkoxy" denotes a $(C_1-C_7)$-alkoxy residue as defined before, wherein one or more hydrogen atoms are replaced by fluorine.

"$(C_1-C_7)$-alkoxy-(ethoxy)$_m$" (m is 1, 2, 3 or 4) denotes a $(C_1-C_7)$-alkoxy residue in the sense of the foregoing definition bound via 1 to 4 —CH$_2$—CH$_2$—O— groups, e.g. 2-meth-oxy-ethoxy.

The term "$C_3$–$C_7$-cycloalkyl" means a cycloalkyl group containing 3 to 7 carbon atoms, such as cyclopropyl, cyclobutyl, cyclopentyl or cyclohexyl.

The term "alkylthio" denotes a $(C_1-C_7)$-alkyl residue in the sense of the foregoing definition bound via an sulfur atom, for example methylsulfanyl.

It will be understood that the above residues may bear substituents, e.g. alkyl in the meaning of $R^2$ may be unsubstituted or substituted by OH; alkoxy in the meaning of $R^2$ may be unsubstituted or substituted by cycloalkyl, e.g. by cyclopropyl, or by alkoxy, e.g. methoxy.

"Carbamoyloxy" means the group —O—CO—NH$_2$.

The expression "six-membered aromatic heterocycle containing 1 to 3 nitrogen atoms" means a six-membered heteroaryl group selected from the group consisting of pyridine, pyridazine, pyrimidine, pyrazine and triazine.

"Pyridine-N-oxide" or "pyridine-1-oxide" means a compound having the formula:

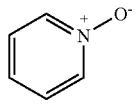

The term "pharmaceutically acceptable addition salt" refers to any salt derived from an inorganic or organic acid or base.

The term "therapeutically effective amount" refers to an amount of at least one AChE inhibitor and mGluR2 antagonist (or that of the compound of formula I) or a pharmaceutically acceptable salt thereof, that modulates the glutamate receptors.

The term "pharmaceutically acceptable excipient" refers to a pharmaceutically acceptable carrier, vehicle, diluent, adjustment, or similar mechanism for delivering a pharmaceutical composition.

In one embodiment the composition comprises a compound of formula I wherein X is a single bond.

In one embodiment the composition of the invention comprises a compound of formula I wherein $R^1$ is hydrogen, halogen, e.g. Cl or F, $(C_1-C_7)$-alkyl, e.g. $CH_3$, fluoro-$(C_1-C_7)$-alkyl, e.g. $CF_3$, fluoro-$(C_1-C_7)$-alkoxy, e.g. $OCF_3$ or $OCH_2CF_3$, pyrrol-1-yl or phenyl, which is unsubstituted or substituted by halogen, e.g. fluorophenyl, e.g. 2-fluorophenyl or 4-fluorophenyl. In another aspect the composition of the invention comprises a compound of formula I wherein $R^1$ is halogen, e.g. Cl or F, fluoro-$(C_1-C_7)$-alkyl, e.g. $CF_3$, fluoro-$(C_1-C_7)$-alkoxy, e.g. $OCF_3$, or phenyl, which is substituted by halogen, e.g. fluorophenyl, e.g. 2-fluorophenyl.

In one embodiment the composition of the invention comprises a compound of formula I wherein $R^2$ is hydrogen, $(C_1-C_7)$-alkyl, e.g. $CH_3$, $CH_2OH$, $CH_2CH_3$ or $CH_2CH_2CH_3$, $(C_2-C_7)$-alkenyl, e.g. ethenyl, $(C_1-C_7)$-alkoxy, e.g. $OCH_3$, $OCH_2CH_3$, $OCH_2CH_2CH_3$, $OCH_2$cyclopropyl or $OCH_2CH_2OCH_3$, halogen, e.g. Cl or F, fluoro-$(C_1-C_7)$-alkyl, e.g. $CF_3$, fluoro-$(C_1-C_7)$-alkoxy, e.g. $OCH_2CF_3$, $(C_3-C_7)$-cycloalkyl, e.g. cyclopropyl, pyrrolidinyl, e.g. pyrrolidin-1-yl, morpholinyl, e.g. morpholin-4-yl, or —NR'R", wherein R' and R" are each independently hydrogen or $(C_1-C_7)$-alkyl, e.g. methyl, propyl or butyl, e.g. $N(CH_3)_2$, $NHCH_2CH(CH_3)_2$, $N(CH_3)CH_2CH_2(CH_3)_2$, $N(CH_3)CH_2(CH_3)_2$ or $N(CH_3)CH_2CH_2CH_3$. In another aspect the composition of the invention comprises a compound of formula I wherein $R^2$ is hydrogen, $(C_1-C_7)$-alkyl, e.g. $CH_3$ or $CH_2CH_3$, $(C_1-C_7)$-alkoxy, e.g. $OCH_3$, $OCH_2CH_3$ or $OCH_2$cyclopropyl, halogen, e.g. Cl, fluoro-$(C_1-C_7)$-alkyl, e.g. $CF_3$, fluoro-$(C_1-C_7)$-alkoxy, e.g. $OCH_2CF_3$, or —NR'R" wherein R' and R" are $(C_1-C_7)$-alkyl, e.g. methyl, e.g. $N(CH_3)_2$.

In one aspect the composition of the invention comprises a compound of formula I wherein $R^3$ is pyridinyl, pyridazinyl, pyrimidinyl, pyrazinyl, [1,2,4]triazinyl or a pyridine-N-oxide, e.g. 1-oxy-pyridinyl, which are unsubstituted or substituted by one or two substituents selected from the group consisting of halogen, fluoro-$(C_1-C_7)$-alkoxy, cyano, amino, $(C_1-C_7)$-alkylamino, $(C_1-C_7)$-dialkylamino, $(C_1-C_7)$-alkoxy-$(C_1-C_7)$-alkylamino, $(C_1-C_7)$-hydroxy-$(C_1-C_7)$-alkylamino, —$(CH_2)_n$—C(O)—OR", —$(CH_2)_n$—C(O)—NR'R", —$(CH_2)_n$—SO$_2$—NR'R", —$(CH_2)_n$—C(NH$_2$)=NR", hydroxy, $(C_1-C_7)$-alkoxy, $(C_1-C_7)$-alkylthio, $C_3-C_7$-cycloalkyl, and $(C_1-C_7)$-alkyl, which is optionally substituted by fluoro, —NR'R", hydroxy, $(C_1-C_7)$-alkoxy, pyrrolidin-1-yl, azetidin-1-yl, cyano or carbamoyloxy, wherein n is 0, 1, 2, 3 or 4; and R' and R" have the meanings specified above.

Examples for pyridinyl are pyridin-2-yl, 6-methylpyridin-2-yl,:pyridin-3-yl, 6-cyanopyridin-3-yl, 6-aminopyridin-3-yl, 6-dimethylaminopyridin-3-yl, 6-methoxypyridin-3-yl, 6-cyclopropylpyridin-3-yl, 6-methylpyridin-3-yl, 2-methylpyridin-3-yl, 4-methylpyridin-3-yl, 2,6-dimethylpyridin-3-yl, 4,6-dimethylpyridin-3-yl, 2-ethylpyridin-3-yl, 6-ethylpyridin-3-yl, 4-methyl-6-ethylpyridin-3-yl, 6-isopropylpyridin-3-yl, 2-isopropylpyridin-3-yl, 4-methyl-6-cyclopropylpyridin-3-yl, pyridin-4-yl, 2-methylpyridin-4-yl, 2-ethylpyridin-4-yl, 2-isopropylpyridin-4-yl, 2-isobutylpyridin-4-yl, 2-hydroxymethylpyridin-4-yl, 2-hydroxymethyl-6-methylpyridin-4-yl, 2-trifluoromethylpyridin-4-yl, 2,3-dimethylpyridin-4-yl, 2,6-dimethylpyridin-4-yl, 3,6-dimethylpyridin-4-yl, 2-ethyl-6-methylpyridin-4-yl, 3-ethyl-6-methylpyridin-4-yl, 2-cyanopyridin-4-yl, 2-cyclopropylpyridin-4-yl, 2-cyclopentylpyridin-4-yl, 2-cyclopropyl-6-methylpyridin-4-yl, 2-morpholin-4-yl-pyridin-4-yl, 2-pyrrolidin-1-yl-pyridin-4-yl, 2-[(isobutyl-methyl-amino)-methyl]-pyridin-4-yl, 2-[(methyl-propyl-amino)-methyl]-pyridin-4-yl, 2-cyclopropylaminomethyl-pyridin-4-yl, 2-pyrrolidin-1-ylmethyl-pyridin-4-yl, 2-azetidin-1-ylmethyl-pyridin-4-yl, 2-methoxymethyl-pyridin-4-yl.

Examples for pyridazinyl are pyridazin-3-yl, 6-methyl-pyridazin-3-yl, 6-methoxy-pyridazin-3-yl and pyridazin-4-yl.

Examples for pyrimidinyl are pyrimidin-2-yl, pyrimidin-4-yl, 2-methylpyrimidin-4-yl, 6-methylpyrimidin-4-yl, 2-amino-6-methylpyrimidin-4-yl, 2-methylamino-6-methylpyrimidin-4-yl, 2-dimethylamino-6-methylpyrimidin-4-yl, 2-hydroxyethylamino-6-methylpyrimidin-4-yl, 2-(2-methoxy-ethylamino)-6-methyl-pyrimidin-4-yl, 2-morpholin-4-yl-6-methyl-pyrimidin-4-yl, 6-aminopyrimidin-4-yl, 6-methylaminopyrimidin-4-yl, 6-dimethylaminopyrimidin-4-yl, 6-(2-methoxy-ethylamino)-pyrimidin-4-yl, and pyrimidin-5-yl.

Examples for pyrazinyl are pyrazin-2-yl and 6-methyl-pyrazin-2-yl.

Examples for [1,2,4]triazinyl are [1,2,4]triazin-3-yl, (5,6-dimethyl-[1,2,4]triazin-3-yl), (3-methyl-[1,2,4]triazin-6-yl and [1,2,4]triazin-6-yl. Examples for a pyridine-N-oxide are 1-oxy-pyridinyl, e.g. 1-oxy-pyridin-3-yl, 1-oxy-pyridin-3-yl), 1-oxy-pyridin-4-yl, 2-methyl-1-oxy-pyridin-4-yl, 2-hydroxymethyl-1-oxy-pyridin-4-yl and 2,6-dimethyl-1-oxy-pyridin-4-yl.

In another aspect the composition of the invention comprises a compound of formula I wherein $R^3$ is pyridinyl or pyrimidinyl, which are unsubstituted or substituted by one or two substituents selected from the group consisting of halogen, fluoro-$(C_1-C_7)$-alkoxy, cyano, amino, $(C_1-C_7)$-alkylamino, $(C_1-C_7)$-dialkylamino, $(C_1-C_7)$-alkoxy-$(C_1-C_7)$-alkylamino, $(C_1-C_7)$-hydroxy-$(C_1-C_7)$-alkylamino, —$(CH_2)_n$—C(O)—OR", —$(CH_2)_n$—C(O)—NR'R", —$(CH_2)_n$—SO$_2$—NR'R", —$(CH_2)_n$—C(NH$_2$)=NR", hydroxy, $(C_1-C_7)$-alkoxy, $(C_1-C_7)$-alkylthio, $C_3-C_7$-cycloalkyl, and $(C_1-C_7)$-alkyl, which is optionally substituted by fluoro, —NR'R", hydroxy, $(C_1-C_7)$-alkoxy, pyrrolidin-1-yl, azetidin-1-yl, cyano or carbamoyloxy, wherein n is 0, 1, 2, 3 or 4; and R' and R" have the meanings specified above. In yet another aspect the composition of the invention comprises a compound of formula I wherein $R^3$ is pyridinyl or pyrimidinyl, which are unsubstituted or substituted by one or two substituents selected from $C_3$–$C_7$-cycloalkyl and $(C_1$–$C_7)$-alkyl, which is optionally substituted by fluoro, —NR'R", hydroxy, $(C_1$–$C_7)$-alkoxy, pyrrolidin-1-yl, azetidin-1-yl, cyano or carbamoyloxy, wherein n is 0, 1, 2, 3 or 4; and R' and R" have the meanings specified above. In still another aspect the composition of the invention comprises a compound of formula I wherein $R^3$ is pyridinyl or pyrimidinyl, which are unsubstituted or substituted by one or two substituents selected from $C_3$–$C_7$-cycloalkyl and $(C_1$–$C_7)$-alkyl, which is unsubstituted or substituted by fluoro or hydroxy. In still another aspect the composition of the invention comprises a compound of formula I wherein $R^3$ is pyridin-3-yl, 6-cyclopropylpyridin-3-yl, pyridin-4-yl, 2-methylpyridin-4-yl, 2-ethylpyridin-4-yl, 2-hydroxymethylpyridin-4-yl, 2,6-dimethylpyridin-4-yl, 2-ethyl-6-methylpyridin-4-yl or 6-methylpyrimidin-4-yl.

In another embodiment the composition of the invention comprises a compound of formula I wherein X is a single bond; Y is —CH= or =N—; $R^1$ is hydrogen, cyano, halogen, $(C_1$–$C_7)$-alkyl, $(C_1$–$C_7)$-alkoxy, fluoro-$(C_1$–$C_7)$-alkyl, fluoro-$(C_1$–$C_7)$-alkoxy, pyrrol-1-yl, or phenyl, which is unsubstituted or substituted by one or two substituents selected from the group consisting of halogen, $(C_1$–$C_7)$-alkyl or fluoro-$(C_1$–$C_7)$-alkyl; $R^2$ is hydrogen, $(C_1$–$C_7)$-alkyl, $(C_2$–$C_7)$-alkenyl, $(C_1$–$C_7)$-alkoxy, halogen, —NR'R", pyrrolidin-1-yl, piperidin-1-yl, morpholine-4-yl, fluoro-$(C_1$–$C_7)$-alkyl, fluoro-$(C_1$–$C_7)$-alkoxy, or $(C_1$–$C_7)$-alkoxy-(ethoxy)$_m$; wherein m is 1, 2, 3 or 4; R' and R" are each independently hydrogen, $(C_1$–$C_7)$-alkyl or $(C_3$–$C_7)$-cycloalkyl; and $R^3$ is a six-membered aromatic heterocycle containing 1 to 3 nitrogen atoms or a pyridine-N-oxide, which rings are unsubstituted or substituted by one or two substituents selected from the group consisting of halogen, fluoro-$(C_1$–$C_7)$-alkyl, fluoro-$(C_1$–$C_7)$-alkoxy, cyano, amino, $(C_1$–$C_7)$-alkylamino, $(C_1$–$C_7)$-dialkylamino, $(C_1$–$C_7)$-alkoxy-$(C_1$–$C_7)$-alkylamino, $(C_1$–$C_7)$-hydroxy-$(C_1$–$C_7)$-alkylamino, —$(CH_2)_n$—C(O)—OR", —$(CH_2)_n$—C(O)—NR'R", —$(CH_2)_n$—SO$_2$—NR'R", —$(CH_2)_n$—C(NH$_2$)=NR", hydroxy, $(C_1$–$C_7)$-alkoxy, $(C_1$–$C_7)$-alkylthio, $C_3$–$C_7$-cycloalkyl and $(C_1$–$C_7)$-alkyl, which is optionally substituted by fluoro, —NR'R", hydroxy, $(C_1$–$C_7)$-alkoxy, pyrrolidin-1-yl, azetidin-1-yl, cyano or carbamoyloxy, wherein n is 0, 1, 2, 3 or 4; and R' and R" have the meanings specified above.

In another embodiment the composition of the invention comprises a compound of formula I wherein X is a single bond; Y is =N—; R' is hydrogen, cyano, halogen, $(C_1$–$C_7)$-alkyl, $(C_1$–$C_7)$-alkoxy, fluoro-$(C_1$–$C_7)$-alkyl, fluoro-$(C_1$–$C_7)$-alkoxy, pyrrol-1-yl, or phenyl, which is unsubstituted or substituted by one or two substituents selected from the group consisting of halogen, $(C_1$–$C_7)$-alkyl or fluoro-$(C_1$–$C_7)$-alkyl; $R^2$ is hydrogen, $(C_1$–$C_7)$-alkyl, $(C_2$–$C_7)$-alkenyl, $(C_1$–$C_7)$-alkoxy, halogen, —NR'R", pyrrolidin-1-yl, piperidin-1-yl, morpholine-4-yl, fluoro-$(C_1$–$C_7)$-alkyl, fluoro-$(C_1$–$C_7)$-alkoxy, or $(C_1$–$C_7)$-alkoxy-(ethoxy)$_m$; wherein m is 1, 2, 3 or 4; R' and R" are each independently hydrogen, $(C_1$–$C_7)$-alkyl or $(C_3$–$C_7)$-cycloalkyl; and $R^3$ is a six-membered aromatic heterocycle containing 1 to 3 nitrogen atoms or a pyridine-N-oxide, which rings are unsubstituted or substituted by one or two substituents selected from the group consisting of halogen, fluoro-$(C_1$–$C_7)$-alkyl, fluoro-$(C_1$–$C_7)$-alkoxy, cyano, amino, $(C_1$–$C_7)$-alkylamino, $(C_1$–$C_7)$-dialkylamino, $(C_1$–$C_7)$-alkoxy-$(C_1$–$C_7)$-alkylamino, $(C_1$–$C_7)$-hydroxy-$(C_1$–$C_7)$-alkylamino, —$(CH_2)_n$—C(O)—OR", —$(CH_2)_n$—C(O)—NR'R", —$(CH_2)_n$—SO$_2$—NR'R", —$(CH_2)_n$—C(NH$_2$)=NR", hydroxy, $(C_1$–$C_7)$-alkoxy, $(C_1$–$C_7)$-alkylthio, $C_3$–$C_7$-cycloalkyl and $(C_1$–$C_7)$-alkyl, which is optionally substituted by fluoro, —NR'R", hydroxy, $(C_1$–$C_7)$-alkoxy, pyrrolidin-1-yl, azetidin-1-yl, cyano or carbamoyloxy, wherein n is 0, 1, 2, 3 or 4; and R' and R" have the meanings specified above.

In another embodiment the composition of the invention comprises a compound of formula I wherein X is a single bond; Y is =N—; $R^1$ is halogen, $(C_1$–$C_7)$-alkyl, $(C_1$–$C_7)$-alkoxy, fluoro-$(C_1$–$C_7)$-alkyl, or phenyl, which is substituted by halogen; $R^2$ is hydrogen, $(C_1$–$C_7)$-alkyl, $(C_1$–$C_7)$-alkoxy, halogen, —NR'R", fluoro-$(C_1$–$C_7)$-alkyl, fluoro-$(C_1$–$C_7)$-alkoxy, wherein R' and R" are each independently $(C_1$–$C_7)$-alkyl; and $R^3$ is pyridinyl which is unsubstituted or substituted by one or two substituents selected from $(C_1$–$C_7)$-alkyl, which is unsubstituted or substituted by hydroxy; and R' and R" have the meanings specified above.

In another embodiment the composition of the invention comprises a compound of formula I wherein X is a single bond; Y is =N—; $R^1$ is fluoro-$(C_1$–$C_7)$-alkyl; $R^2$ is $(C_1$–$C_7)$-alkyl; and $R^3$ is pyridinyl which is unsubstituted or substituted by one or two substituents selected from $(C_1$–$C_7)$-alkyl, which is unsubstituted or substituted by hydroxy; and R' and R" have the meanings specified above.

In still another embodiment the composition of the invention comprises a compound of formula I wherein X is a single bond; Y is =N—; $R^1$ is halogen, $(C_1$–$C_7)$-alkyl, $(C_1$–$C_7)$-alkoxy, fluoro-$(C_1$–$C_7)$-alkyl, or phenyl, which is substituted by halogen; $R^2$ is hydrogen, $(C_1$–$C_7)$-alkyl, $(C_1$–$C_7)$-alkoxy, halogen, —NR'R", fluoro-$(C_1$–$C_7)$-alkyl, fluoro-$(C_1$–$C_7)$-alkoxy, wherein R' and R" are each independently $(C_1$–$C_7)$-alkyl; and $R^3$ is pyridinyl which is unsubstituted or substituted by $(C_1$–$C_7)$-alkyl.

In another embodiment the composition of the invention comprises a compound of formula I wherein X is a single bond; Y is =N—; $R^1$ is fluoro-$(C_1$–$C_7)$-alkyl; $R^2$ is $(C_1$–$C_7)$-alkyl; and $R^3$ is pyridinyl which is unsubstituted or substituted by $(C_1$–$C_7)$-alkyl. In yet another embodiment the composition of the invention comprises a compound of formula I wherein X is a single bond, Y is =N—, $R^1$ is CF$_3$, $R^2$ is CH$_3$ and $R^3$ is pyridin-3-yl, pyridin-4-yl, 2-methylpyridin-4-yl or 2,6-dimethylpyridin-4-yl.

In one embodiment the composition of the invention comprises a compound of formula I wherein X is a single bond; Y is —CH=; $R^1$ is hydrogen, cyano, halogen, $(C_1$–$C_7)$-alkyl, $(C_1$–$C_7)$-alkoxy, fluoro-$(C_1$–$C_7)$-alkyl, fluoro-$(C_1$–$C_7)$-alkoxy, pyrrol-1-yl, or phenyl, which is unsubstituted or substituted by one or two substituents selected from the group consisting of halogen, $(C_1$–$C_7)$-alkyl or fluoro-$(C_1$–$C_7)$-alkyl; $R^2$ is hydrogen, $(C_1$–$C_7)$-alkyl, $(C_2$–$C_7)$-alkenyl, $(C_1$–$C_7)$-alkoxy, halogen, —NR'R", pyrrolidin-1-yl, piperidin-1-yl, morpholine-4-yl, fluoro-$(C_1$–$C_7)$-alkyl, fluoro-$(C_1$–$C_7)$-alkoxy, or $(C_1$–$C_7)$-alkoxy-(ethoxy)$_m$; wherein m is 1, 2, 3 or 4; R' and R" are each independently hydrogen, $(C_1$–$C_7)$-alkyl or $(C_3$–$C_7)$-cycloalkyl; and $R^3$ is a six-membered aromatic heterocycle containing 1 to 3 nitrogen atoms or a pyridine-N-oxide, which rings are unsubstituted or substituted by one or two substituents selected from the group consisting of halogen, fluoro-$(C_1$–$C_7)$-alkyl, fluoro-$(C_1$–$C_7)$-alkoxy, cyano, amino, $(C_1$–$C_7)$-alkylamino, $(C_1$–$C_7)$-dialkylamino, $(C_1$–$C_7)$-alkoxy-$(C_1$–$C_7)$-alkylamino, $(C_1$–$C_7)$-hydroxy-$(C_1$–$C_7)$-alkylamino, —$(CH_2)_n$—C(O)—OR", —$(CH_2)_n$—C(O)—NR'R", —$(CH_2)_n$—SO$_2$—NR'R", —$(CH_2)_n$—C(NH$_2$)=NR", hydroxy, $(C_1$–$C_7)$-alkoxy, $(C_1$–$C_7)$-alkylthio, $C_3$–$C_7$-cycloalkyl and $(C_1$–$C_7)$-alkyl, which is optionally substituted by fluoro, —NR'R", hydroxy, $(C_1$–$C_7)$-alkoxy, pyrrolidin-1-yl, azetidin-1-yl, cyano or carbamoyloxy, wherein n is 0, 1, 2, 3 or 4; and R' and R" have the meanings specified above.

In another embodiment the composition of the invention comprises a compound of formula I wherein X is a single bond; Y is —CH=; $R^1$ is halogen, ($C_1$–$C_7$)-alkyl, ($C_1$–$C_7$)-alkoxy, fluoro-($C_1$–$C_7$)-alkyl, or phenyl, which is substituted by one or two substituents consisting of halogen; $R^2$ is hydrogen, ($C^1$–$C_7$)-alkyl, ($C_1$–$C_7$)-alkoxy, halogen, —NR'R", fluoro-($C_1$–$C_7$)-alkyl, fluoro-($C_1$–$C_7$)-alkoxy, wherein R' and R" are each independently ($C_1$–$C_7$)-alkyl; and $R^3$ is a six-membered aromatic heterocycle containing 1 to 3 nitrogen atoms or a pyridine-N-oxide, which rings are unsubstituted or substituted by one or two substituents selected from the group consisting of halogen, fluoro-($C_1$–$C_7$)-alkyl, fluoro-($C_1$–$C_7$)-alkoxy, cyano, amino, ($C_1$–$C_7$)-alkylamino, ($C_1$–$C_7$)-dialkylamino, ($C_1$–$C_7$)-alkoxy-($C_1$–$C_7$)-alkylamino, ($C_1$–$C_7$)-hydroxy-($C_1$–$C_7$)-alkylamino, —$(CH_2)_n$—C(O)—OR", —$(CH_2)_n$—C(O)—NR'R", —$(CH_2)_n$—$SO_2$—NR'R", —$(CH_2)_n$—C($NH_2$)=NR", hydroxy, ($C_1$–$C_7$)-alkoxy, ($C_1$–$C_7$)-alkylthio, $C_3$–$C_7$-cycloalkyl and ($C_1$–$C_7$)-alkyl, which is optionally substituted by fluoro, —NR'R", hydroxy, ($C_1$–$C_7$)-alkoxy, pyrrolidin-1-yl, azetidin-1-yl, cyano or carbamoyloxy, wherein n is 0, 1, 2, 3 or 4; and R' and R" have the meanings specified above.

In another embodiment the composition of the invention comprises a compound of formula I wherein X is a single bond; Y is —CH=; $R^1$ is hydrogen, cyano, halogen, ($C_1$–$C_7$)-alkyl, ($C_1$–$C_7$)-alkoxy, fluoro-($C_1$–$C_7$)-alkyl, fluoro-($C_1$–$C_7$)-alkoxy, pyrrol-1-yl, or phenyl, which is unsubstituted or substituted by one or two substituents selected from the group consisting of halogen, ($C_1$–$C_7$)-alkyl or fluoro-($C_1$–$C_7$)-alkyl; $R^2$ is hydrogen, ($C_1$–$C_7$)-alkyl, ($C_2$–$C_7$)-alkenyl, ($C_1$–$C_7$)-alkoxy, halogen, —NR'R", pyrrolidin-1-yl, piperidin-1-yl, morpholine-4-yl, fluoro-($C_1$–$C_7$)-alkyl, fluoro-($C_1$–$C_7$)-alkoxy, or ($C_1$–$C_7$)-alkoxy-(ethoxy)$_m$; wherein m is 1, 2, 3 or 4; R' and R" are each independently hydrogen, ($C_1$–$C_7$)-alkyl or ($C_3$–$C_7$)-cycloalkyl; and $R^3$ is pyridinyl or pyrimidinyl, which are unsubstituted or substituted by one or two substituents selected from the group consisting of halogen, fluoro-($C_1$–$C_7$)-alkyl, fluoro-($C_1$–$C_7$)-alkoxy, cyano, amino, ($C_1$–$C_7$)-alkylamino, ($C_1$–$C_7$)-dialkylamino, ($C_1$–$C_7$)-alkoxy-($C_1$–$C_7$)-alkylamino, ($C_1$–$C_7$)-hydroxy-($C_1$–$C_7$)-alkylamino, —$(CH_2)_n$—C(O)—OR", —$(CH_2)_n$—C(O)—NR'R", —$(CH_2)_n$—$SO_2$—NR'R", —$(CH_2)_n$—C($NH_2$)=NR", hydroxy, ($C_1$–$C_7$)-alkoxy, ($C_1$–$C_7$)-alkylthio, $C_3$–$C_7$-cycloalkyl and ($C_1$–$C_7$)-alkyl, which is optionally substituted by fluoro, —NR'R", hydroxy, ($C_1$–$C_7$)-alkoxy, pyrrolidin-1-yl, azetidin-1-yl, cyano or carbamoyloxy, wherein n is 0, 1, 2, 3 or 4; and R' and R" have the meanings specified above.

In still another embodiment the composition of the invention comprises a compound of formula I wherein X is a single bond; Y is —CH=; $R^1$ is hydrogen, cyano, halogen, ($C_1$–$C_7$)-alkyl, ($C_1$–$C_7$)-alkoxy, fluoro-($C_1$–$C_7$)-alkyl, fluoro-($C_1$–$C_7$)-alkoxy, pyrrol-1-yl, or phenyl, which is unsubstituted or substituted by one or two substituents selected from the group consisting of halogen, ($C_1$–$C_7$)-alkyl or fluoro-($C_1$–$C_7$)-alkyl; $R^2$ is hydrogen, ($C_1$–$C_7$)-alkyl, ($C_2$–$C_7$)-alkenyl, ($C_1$–$C_7$)-alkoxy, halogen, —NR'R", pyrrolidin-1-yl, piperidin-1-yl, morpholine-4-yl, fluoro-($C_1$–$C_7$)-alkyl, fluoro-($C_1$–$C_7$)-alkoxy, or ($C_1$–$C_7$)-alkoxy-(ethoxy)$_m$; wherein m is 1, 2, 3 or 4; R' and R" are each independently hydrogen, ($C_1$–$C_7$)-alkyl or ($C_3$–$C_7$)-cycloalkyl; and $R^3$ is pyridinyl or pyrimidinyl, which are unsubstituted or substituted by one or two substituents selected from the group consisting of $C_3$–$C_7$-cycloalkyl and ($C_1$–$C_7$)-alkyl, which is unsubstituted or substituted by hydroxy.

In still another embodiment the composition of the invention comprises a compound of formula I wherein X is a single bond; Y is —CH=; $R^1$ is halogen, ($C_1$–$C_7$)-alkyl, ($C_1$–$C_7$)-alkoxy, fluoro-($C_1$–$C_7$)-alkyl, or phenyl, which is unsubstituted or substituted by one or two substituents selected from the group consisting of halogen; $R^2$ is hydrogen, ($C_1$–$C_7$)-alkyl, ($C_2$–$C_7$)-alkenyl, ($C_1$–$C_7$)-alkoxy, halogen, —NR'R", pyrrolidin-1-yl, piperidin-1-yl, morpholine-4-yl, fluoro-($C_1$–$C_7$)-alkyl, fluoro-($C_1$–$C_7$)-alkoxy, or ($C_1$–$C_7$)-alkoxy-(ethoxy)$_m$; wherein m is 1, 2, 3 or 4; R' and R" are each independently hydrogen, ($C_1$–$C_7$)-alkyl or ($C_3$–$C_7$)-cycloalkyl; and $R^3$ is pyridinyl or pyrimidinyl, which are unsubstituted or substituted by one or two substituents selected from the group consisting of $C_3$–$C_7$-cycloalkyl and ($C_1$–$C_7$)-alkyl, which is unsubstituted or substituted by hydroxy.

In still another embodiment the composition of the invention comprises a compound of formula I wherein X is a single bond; Y is —CH=; $R^1$ is hydrogen, cyano, halogen, ($C_1$–$C_7$)-alkyl, ($C_1$–$C_7$)-alkoxy, fluoro-($C_1$–$C_7$)-alkyl, fluoro-($C_1$–$C_7$)-alkoxy, pyrrol-1-yl, or,phenyl, which is unsubstituted or substituted by one or two substituents selected from the group consisting of halogen, ($C_1$–$C_7$)-alkyl or fluoro-($C_1$–$C_7$)-alkyl; $R^2$ is hydrogen, ($C_1$–$C_7$)-alkyl, ($C_1$–$C_7$)-alkoxy, halogen, —NR'R", fluoro-($C_1$–$C_7$)-alkyl, fluoro-($C_1$–$C_7$)-alkoxy; wherein R' and R" are each independently hydrogen, ($C_1$–$C_7$)-alkyl or ($C_3$–$C_7$)-cycloalkyl; and $R^3$ is pyridinyl or pyrimidinyl, which are unsubstituted or substituted by one or two substituents selected from the group consisting of $C_3$–$C_7$-cycloalkyl and ($C_1$–$C_7$)-alkyl, which is unsubstituted or substituted by hydroxy.

In still another embodiment the composition of the invention comprises a compound of formula I wherein X is a single bond; Y is —CH=; $R^1$ is halogen, ($C_1$–$C_7$)-alkyl, ($C_1$–$C_7$)-alkoxy, fluoro-($C_1$–$C_7$)-alkyl, fluoro-($C_1$–$C_7$)-alkoxy, or phenyl, which is substituted by one or two substituents selected from the group consisting of halogen; $R^2$ is hydrogen, ($C_1$–$C_7$)-alkyl, ($C_1$–$C_7$)-alkoxy, halogen, —NR'R", fluoro-($C_1$–$C_7$)-alkyl, fluoro-($C_1$–$C_7$)-alkoxy; wherein R' and R" are each independently ($C_1$–$C_7$)-alkyl; and $R^3$ is pyridinyl or pyrimidinyl, which are unsubstituted or substituted by one or two substituents selected from the group consisting of $C_3$–$C_7$-cycloalkyl and ($C_1$–$C_7$)-alkyl, which is unsubstituted or substituted by hydroxy.

In yet another embodiment the composition of the invention comprises a compound of formula I wherein X is a single bond; Y is —CH=; $R^1$ is Cl or F, $CH_3$, $CF_3$, $OCF_3$, or phenyl, which is substituted by fluoro; $R^2$ is hydrogen, methyl, ethyl, cyclopropylmethoxy, methoxyethoxy, Cl, $N(CH_3)_2$, $CF_3$, $OCH_2CF_3$; and $R^3$ is pyridinyl or pyrimidinyl, which are unsubstituted or substituted by one or two substituents selected from the group consisting of cyclopropyl, ethyl and methyl which is unsubstituted or substituted by hydroxy. In still another embodiment the composition of the invention comprises a compound of formula I wherein X is a single bond; Y is —CH=; $R^1$ is Cl or F, $CH_3$, $CF_3$, $OCF_3$, or phenyl, which is substituted by fluoro; $R^2$ is hydrogen, methyl, ethyl, cyclopropylmethoxy, methoxyethoxy, Cl, $N(CH_3)_2$, $CF_3$, $OCH_2CF_3$; and $R^3$ is pyrimidinyl or pyridinyl which is unsubstituted or substituted by one or two substituents selected from the group consisting of ethyl and methyl which is unsubstituted or substituted by hydroxy.

In one embodiment the composition of the invention comprises a compound of formula I selected from:

8-methyl-4-(3-pyridin-3-yl-phenyl)-7-trifluoromethyl-1,3-dihydro-benzo[b][1,4]diazepin-2-one, 8-methyl-4-[3-(2-methyl-pyridin-4-yl)-phenyl]-7-trifluoromethyl-1,3-dihydro benzo[b][1,4]diazepin-2-one, 4-(3-pyridin-3-yl-phenyl)-7-(2,2,2-trifluoro-ethoxy)-1,3-dihydro-benzo[b][1,4]diazepin-2-one, 4-[3-(2,6-dimethyl-pyridin-4-yl)-phenyl]-8-methyl-7-trifluoromethyl-1,3-dihydro benzo[b][1,4]diazepin-2-one,
7,8-dichloro-4-(3-pyridin-3-yl-phenyl)-1,3-dihydro-benzo[b][1,4]diazepin-2-one,
8-chloro-4-(3-pyridin-4-yl-phenyl)-1,3-dihydro-benzo[b][1,4]diazepin-2-one,
8-chloro-4-(3-pyridin-4-yl-phenyl)-1,3-dihydro-benzo[b][1,4]diazepin-2-one,
7,8-dichloro-4-(3-pyridin-4-yl-phenyl)-1,3-dihydro-benzo[b][1,4]diazepin-2-one,
8-chloro-7-methyl-4-(3-pyridin-3-yl-phenyl)-1,3-dihydro-benzo[b][1,4]diazepin-2-one,
8-chloro-4-(3-pyridin-3-yl-phenyl)-1,3-dihydro-benzo[b][1,4]diazepin-2-one,
8-chloro-4-[3-(6-methyl-pyridin-3-yl)-phenyl]-1,3-dihydro-benzo[b][1,4]diazepin-2-one,
8-chloro-4-[3-(2-methyl-pyridin-3-yl)-phenyl]-1,3-dihydro-benzo[b][1,4]diazepin-2-one,
8-chloro-7-methyl-4-(3-pyridin-4-yl-phenyl)-1,3-dihydro-benzo[b][1,4]diazepin-2-one,
7,8-dichloro-4-[3-(2-methyl-pyridin-4-yl)-phenyl]-1,3-dihydro-benzo[b][1,4]diazepin-2-one,
8-chloro-7-methyl-4-[3-(2-methyl-pyridin-4-yl)-phenyl]-1,3-dihydro-benzo[b][1,4]diazepin-2-one,
8-fluoro-4-[3-(2-methyl-pyridin-4-yl)-phenyl]-1,3-dihydro-benzo[b][1,4]diazepin-2-one,
8-chloro-4-[3-(2-methyl-pyridin-4-yl)-phenyl]-7-trifluoromethyl-1,3-dihydro benzo[b][1,4]diazepin-2-one,
8-chloro-4-[3-(2,6-dimethyl-pyridin-4-yl)-phenyl]-7-methyl-1,3-dihydro-benzo-[b][1,4]diazepin-2-one,
7,8-dichloro-4-[3-(2,6-dimethyl-pyridin-4-yl)-phenyl]-1,3-dihydro-benzo[b][1,4]diazepin-2-one,
7-dimethylamino-4-(3-pyridin-3-yl-phenyl)-8-trifluoromethyl-1,3-dihydro-benzo-[b][1,4]diazepin-2-one,
7-dimethylamino-4-(3-pyridin-4-yl-phenyl)-8-trifluoromethyl-1,3-dihydro-benzo-[b][1,4]diazepin-2-one,
4-(3-pyridin-4-yl-phenyl)-8-trifluoromethyl-1,3-dihydro-benzo[b][1,4]diazepin-2-one,
4-(3-pyridin-3-yl-phenyl)-8-trifluoromethyl-1,3-dihydro-benzo[b][1,4]diazepin-2-one,
4-(3-pyridin-3-yl-phenyl)-7-(2,2,2-trifluoro-ethoxy)-8-trifluoromethyl-1,3-dihydro-benzo[b][1,4]diazepin-2-one,
7-ethoxy-4-(3-pyridin-4-yl-phenyl)-8-trifluoromethyl-1,3-dihydro-benzo[b][1,4]diazepin-2-one,
4-(3-pyridin-4-yl-phenyl)-7-(2,2,2-trifluoro-ethoxy)-8-trifluoromethyl-1,3-dihydro-benzo[b][1,4]diazepin-2-one,
7-methyl-4-(3-pyridin-4-yl-phenyl)-8-trifluoromethyl-1,3-dihydro-benzo[b][1,4]diazepin-2-one,
8-methyl-4-(3-pyridin-4-yl-phenyl)-7-trifluoromethyl-1,3-dihydro-benzo[b][1,4]diazepin-2-one,
7-chloro-4-(3-pyridin-4-yl-phenyl)-8-trifluoromethyl-1,3-dihydro-benzo[b][1,4]diazepin-2-one,
7-methyl-4-[3-(2-methyl-pyridin-4-yl)-phenyl]-8-trifluoromethyl-1,3-dihydro benzo[b][1,4]diazepin-2-one,
4-[3-(2-methyl-pyridin-4-yl)-phenyl]-8-trifluoromethyl-1,3-dihydro benzo[b][1,4]diazepin-2-one,
7-dimethylamino-4-[3-(2-methyl-pyridin-4-yl)-phenyl]-8-trifluoromethyl-1,3-dihydro benzo[b][1,4]diazepin-2-one,
4-[3-(2,6-dimethyl-pyridin-4-yl)-phenyl]-7-methyl-8-trifluoromethyl-1,3-dihydro benzo[b][1,4]diazepin-2-one,
4-[3-(2,6-dimethyl-pyridin-4-yl)-phenyl]-8-trifluoromethyl-1,3-dihydro benzo-[b][1,4]diazepin-2-one,
7-chloro-4-[3-(2,6-dimethyl-pyridin-4-yl)-phenyl]-8-trifluoromethyl-1,3-dihydro benzo[b][1,4]diazepin-2-one,
4-[3-(2,6-dimethyl-pyridin-4-yl)-phenyl]-7-(2,2,2-trifluoro-ethoxy)-8-trifluoromethyl-1,3-dihydro-benzo[b][1,4]diazepin-2-one,
4-[3-(2,6-dimethyl-pyridin-4-yl)-phenyl]-7-ethoxy-8-trifluoromethyl-1,3-dihydro-benzo[b][1,4]diazepin-2-one,
4-[3-(2-ethyl-pyridin-4-yl)-phenyl]-7-methyl-8-trifluoromethyl-1,3-dihydro benzo[b][1,4]diazepin-2-one,
4-[3-(6-cyclopropyl-pyridin-3-yl)-phenyl]-8-trifluoromethyl-1,3-dihydro-benzo-[b][1,4]diazepin-2-one,
7-methyl-4-(3-pyridin-3-yl-phenyl)-8-trifluoromethyl-1,3-dihydro-benzo[b][1,4]diazepin-2-one,
7-methoxy-4-(3-pyridin-3-yl-phenyl)-8-trifluoromethyl-1,3-dihydro-benzo[b][1,4]diazepin-2-one,
7-ethoxy-4-(3-pyridin-3-yl-phenyl)-8-trifluoromethyl-1,3-dihydro-benzo[b][1,4]diazepin-2-one,
7-cyclopropylmethoxy-4-[3-(2-methyl-pyridin-4-yl)-phenyl]-8-trifluoromethyl-1,3-dihydro-benzo[b][1,4]diazepin-2-one,
7-ethyl-4-[3-(2-methyl-pyridin-4-yl)-phenyl]-8-trifluoromethyl-1,3-dihydro-benzo[b][1,4]diazepin-2-one,
4-[3-(2,6-dimethyl-pyridin-4-yl)-phenyl]-7-ethyl-8-trifluoromethyl-1,3-dihydro-benzo[b][1,4]diazepin-2-one,
4-[3-(2-ethyl-6-methyl-pyridin-4-yl)-phenyl]-7-methyl-8-trifluoromethyl-1,3-dihydro-benzo[b][1,4]diazepin-2-one,
4-[3-(2-hydroxymethyl-pyridin-4-yl)-phenyl]-7-methyl-8-trifluoromethyl-1,3-dihydro benzo[b][1,4]diazepin-2-one,
8-(2-fluoro-phenyl)-4-[3-(2-methyl-pyridin-3-yl)-phenyl]-1,3-dihydro-benzo[b][1,4]diazepin-2-one,
8-(2-fluoro-phenyl)-4-(3-pyridin-4-yl-phenyl)-1,3-dihydro-benzo[b][1,4]diazepin-2-one,
8-(2-fluoro-phenyl)-4-(3-pyridin-3-yl-phenyl)-1,3-dihydro-benzo[b][1,4]diazepin-2-one,
8-(2-fluoro-phenyl)-4-[3-(2-methyl-pyridin-4-yl)-phenyl]-1,3-dihydro-benzo[b][1,4]diazepin-2-one,
4-[3-(2-methyl-pyridin-4-yl)-phenyl]-8-trifluoromethoxy-1,3-dihydro-benzo[b][1,4]diazepin-2-one,
8-chloro-7-methyl-4-(3-pyrazin-2-yl-phenyl)-1,3-dihydro-benzo[b][1,4]diazepin-2-one,
7-methyl-4-(3-pyrazin-2-yl-phenyl)-8-trifluoromethyl-1,3-dihydro-benzo[b][1,4]diazepin-2-one,
7-(methyl-propyl-amino)-4-(3-pyrazin-2-yl-phenyl)-8-trifluoromethyl-1,3-dihydro-benzo[b][1,4]diazepin-2-one,
8-chloro-7-methyl-4-(3-pyridazin-4-yl-phenyl)-1,3-dihydro-benzo[b][1,4]diazepin-2-one,
7-methyl-4-(3-pyridazin-4-yl-phenyl)-8-trifluoromethyl-1,3-dihydro-benzo[b][1,4]diazepin-2-one,
8-(2-fluoro-phenyl)-4-(3-pyrimidin-5-yl-phenyl)-1,3-dihydro-benzo[b][1,4]diazepin-2-one,
4-[3-(6-methyl-pyrimidin-4-yl)-phenyl]-8-trifluoromethyl-1,3-dihydro-benzo-[b][1,4]diazepin-2-one,
4-[2,3']bipyridinyl-4-yl-7-methyl-8-trifluoromethyl-1,3-dihydro-benzo[b][1,4]diazepin-2-one, and
7-methyl-4-(2'-methyl-[2,4']bipyridinyl-4-yl)-8-trifluoromethyl-1,3-dihydro-benzo[b][1,4]diazepin-2-one.

In another embodiment the composition of the present invention comprises a compound of formula I selected from
7-dimethylamino-4-(3-pyridin-3-yl-phenyl)-8-trifluoromethyl-1,3-dihydro-benzo-[b][1,4]diazepin-2-one,
7-dimethylamino-4-(3-pyridin-4-yl-phenyl)-8-trifluoromethyl-1,3-dihydro-benzo-[b][1,4]diazepin-2-one,
4-(3-pyridin-4-yl-phenyl)-8-trifluoromethyl-1,3-dihydro-benzo[b][1,4]diazepin-2-one,
8-chloro-4-(3-pyridin-4-yl-phenyl)-1,3-dihydro-benzo[b][1,4]diazepin-2-one,
4-(3-pyridin-3-yl-phenyl)-8-trifluoromethyl-1,3-dihydro-benzo[b][1,4]diazepin-2-one,
4-(3-pyridin-3-yl-phenyl)-7-(2,2,2-trifluoro-ethoxy)-8-trifluoromethyl-1,3-dihydro-benzo[b][1,4]diazepin-2-one,
7-ethoxy-4-(3-pyridin-4-yl-phenyl)-8-trifluoromethyl-1,3-dihydro-benzo[b][1,4]diazepin-2-one,
7-ethoxy-4-[3-(2-methyl-pyridin-4-yl)-phenyl]-8-trifluoromethyl-1,3-dihydro-benzo[b][1,4]diazepin-2-one,
7-methyl-4-(3-pyridin-4-yl-phenyl)-8-trifluoromethyl-1,3-dihydro-benzo[b][1,4]diazepin-2-one, 8-chloro-7-methyl-4-(3-pyridin-4-yl-phenyl)-1,3-dihydro-benzo[b][1,4]diazepin-2-one,
7-chloro-4-(3-pyridin-4-yl-phenyl)-8-trifluoromethyl-1,3-dihydro-benzo[b][1,4]diazepin-2-one,
7,8-dichloro-4-[3-(2-methyl-pyridin-4-yl)-phenyl]-1,3-dihydro-benzo[b][1,4]diazepin-2-one,
8-(2-fluoro-phenyl)-4-[3-(2-methyl-pyridin-4-yl)-phenyl]-1,3-dihydro-benzo[b][1,4]diazepin-2-one,
8-chloro-7-methyl-4-[3-(2-methyl-pyridin-4-yl)-phenyl]-1,3-dihydro-benzo[b][1,4]diazepin-2-one,
7-methyl-4-[3-(2-methyl-pyridin-4-yl)-phenyl]-8-trifluoromethyl-1,3-dihydro-benzo[b][1,4]diazepin-2-one,
4-[3-(2-methyl-pyridin-4-yl)-phenyl]-8-trifluoromethyl-1,3-dihydro-benzo[b][1,4]diazepin-2-one,
8-methyl-4-[3-(2-methyl-pyridin-4-yl)-phenyl]-7-trifluoromethyl-1,3-dihydro benzo[b][1,4]diazepin-2-one,
8-fluoro-4-[3-(2-methyl-pyridin-4-yl)-phenyl]-1,3-dihydro-benzo[b][1,4]diazepin-2-one,
8-chloro-4-[3-(2-methyl-pyridin-4-yl)-phenyl]-7-trifluoromethyl-1,3-dihydro benzo[b][1,4]diazepin-2-one,
8-chloro-4-[3-(2,6-dimethyl-pyridin-4-yl)-phenyl]-7-methyl-1,3-dihydro-benzo-[b][1,4]diazepin-2-one,
4-[3-(2,6-dimethyl-pyridin-4-yl)-phenyl]-7-methyl-8-trifluoromethyl-1,3-dihydro-benzo[b][1,4]diazepin-2-one,
4-[3-(2,6-dimethyl-pyridin-4-yl)-phenyl]-8-trifluoromethyl-1,3-dihydro benzo[b][1,4]diazepin-2-one,
4-[3-(2,6-dimethyl-pyridin-4-yl)-phenyl]-8-methyl-7-trifluoromethyl-1,3-dihydro-benzo[b][1,4]diazepin-2-one,
7-chloro-4-[3-(2,6-dimethyl-pyridin-4-yl)-phenyl]-8-trifluoromethyl-1,3-dihydro-benzo[b][1,4]diazepin-2-one,
7,8-dichloro-4-[3-(2,6-dimethyl-pyridin-4-yl)-phenyl]-1,3-dihydro-benzo[b][1,4]diazepin-2-one,
4-[3-(2,6-dimethyl-pyridin-4-yl)-phenyl]-7-(2,2,2-trifluoro-ethoxy)-8-trifluoromethyl-1,3-dihydro-benzo[b][1,4]diazepin-2-one,
4-[3-(2,6-dimethyl-pyridin-4-yl)-phenyl]-7-ethoxy-8-trifluoromethyl-1,3-dihydro-benzo[b][1,4]diazepin-2-one,
4-[3-(2-ethyl-pyridin-4-yl)-phenyl]-7-methyl-8-trifluoromethyl-1,3-dihydro-benzo[b][1,4]diazepin-2-one,
4-[3-(6-cyclopropyl-pyridin-3-yl)-phenyl]-8-trifluoromethyl-1,3-dihydro-benzo-[b][1,4]diazepin-2-one,
7-methyl-4-(3-pyridin-3-yl-phenyl)-8-trifluoromethyl-1,3-dihydro-benzo[b][1,4]diazepin-2-one,
7-methoxy-4-(3-pyridin-3-yl-phenyl)-8-trifluoromethyl-1,3-dihydro-benzo-[b][1,4]diazepin-2-one,
7-ethoxy-4-(3-pyridin-3-yl-phenyl)-8-trifluoromethyl-1,3-dihydro-benzo[b][1,4]diazepin-2-one,
4-[3-(2-methyl-pyridin-4-yl)-phenyl]-8-trifluoromethoxy-1,3-dihydro-benzo[b][1,4]diazepin-2-one,
7-cyclopropylmethoxy-4-[3-(2-methyl-pyridin-4-yl)-phenyl]-8-trifluoromethyl-1,3-dihydro-benzo[b][1,4]diazepin-2-one,
7-ethyl-4-[3-(2-methyl-pyridin-4-yl)-phenyl]-8-trifluoromethyl-1,3-dihydro-benzo[b][1,4]diazepin-2-one,
4-[3-(2,6-dimethyl-pyridin-4-yl)-phenyl]-7-ethyl-8-trifluoromethyl-1,3-dihydro-benzo[b][1,4]diazepin-2-one,
4-[3-(2-ethyl-6-methyl-pyridin-4-yl)-phenyl]-7-methyl-8-trifluoromethyl-1,3-dihydro-benzo[b][1,4]diazepin-2-one,
4-[3-(2-hydroxymethyl-pyridin-4-yl)-phenyl]-7-methyl-8-trifluoromethyl-1,3-dihydro benzo[b][1,4]diazepin-2-one,
4-[2,3']bipyridinyl-4-yl-7-methyl-8-trifluoromethyl-1,3-dihydro-benzo[b][1,4]diazepin-2-one,
7-methyl-4-(2'-methyl-[2,4']bipyridinyl-4-yl)-8-trifluoromethyl-1,3-dihydro-benzo[b][1,4]diazepin-2-one, and
4-[3-(6-methyl-pyrimidin-4-yl)-phenyl]-8-trifluoromethyl-1,3-dihydro-benzo[b][1,4]diazepin-2-one.

In one embodiment the present invention is directed to a pharmaceutical composition comprising 4-[3-(2,6-dimethyl-pyridin-4-yl)-phenyl]-7-methyl-8-trifluoromethyl-1,3-dihydro benzo[b][1,4]diazepin-2-one and donepezil hydrochloride.

The compounds of general formula I and their pharmaceutically acceptable salts can be manufactured according to a process, which comprises a) reacting a compound of formula II

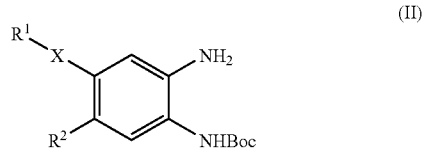

with a compound of formula IV or IVa

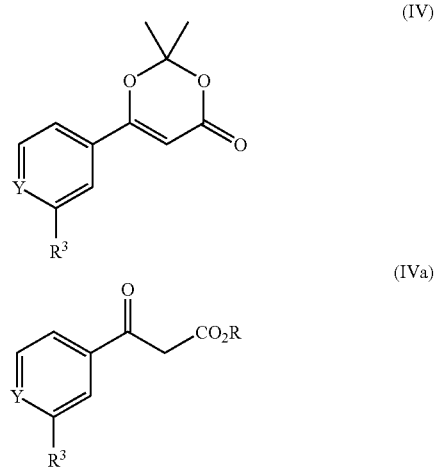

wherein R is ethyl or butyl, to a compound of formula III

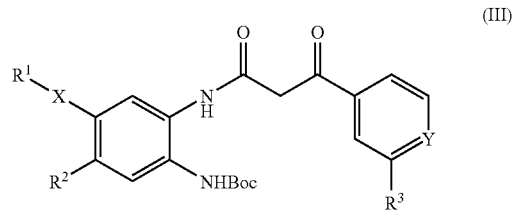

which subsequently undergoes deprotection of the amino group and cyclization, and, if desired,
converting the compound obtained into a pharmaceutically acceptable acid addition salt.

In more detail, according to scheme A, compounds of general formula I, in which X, Y, $R^1$, $R^2$ and $R^3$ are as described above, can be prepared from compounds of general formula II via an acylation-deprotection-cyclization sequence:

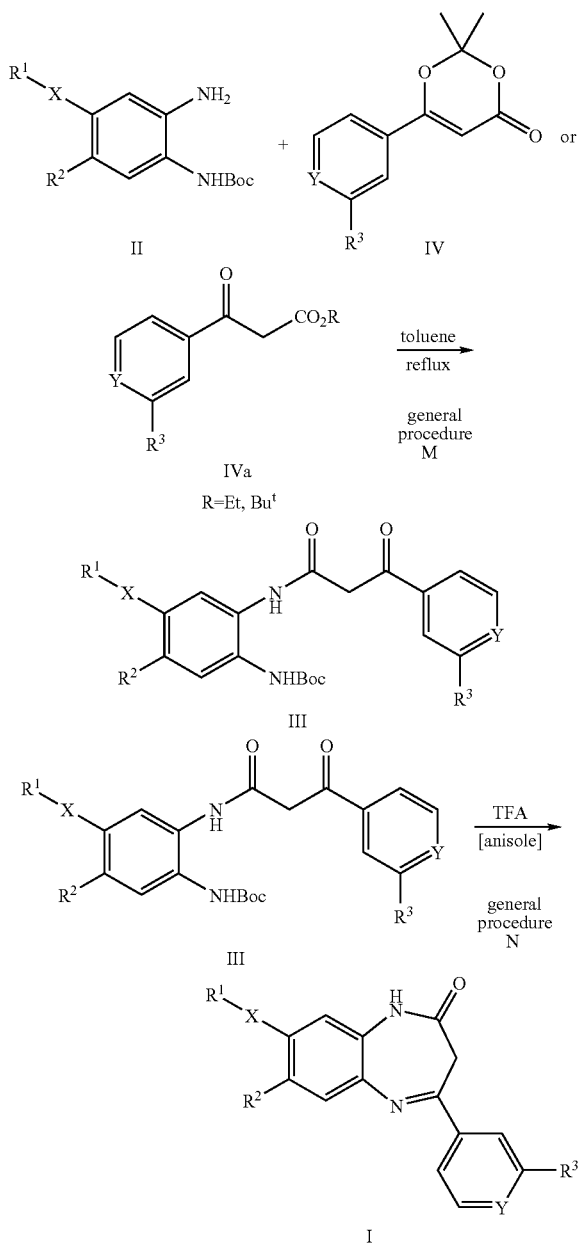

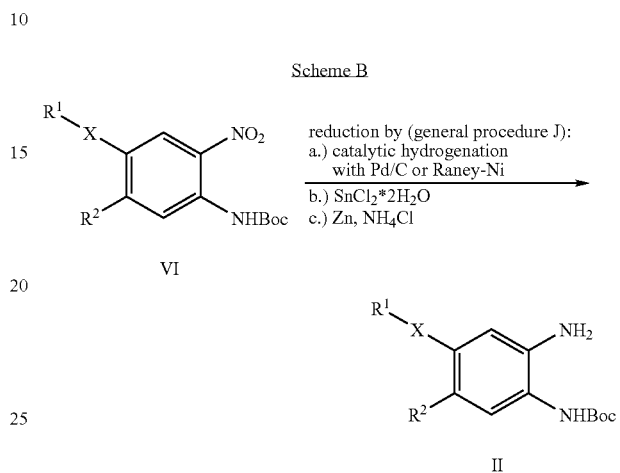

Reacting compounds of general formula II with a dioxinone IV, in which Y and R³ are as described above, in an inert solvent such as toluene or xylene at elevated temperatures, preferably between 80° C. and 160° C., gives rise to compounds of general formula III. Alternatively, compounds of general formula III can also be prepared by for example reaction of a compound of general formula II with a beta-ketoester (general formula IVa), in which Y and R³ are as described above, using the same conditions as described for the reaction with the dioxinones.

Afterwards, cleaving the BOC (tert-butoxycarbonyl) protecting group in compounds of general formula III and concomitant cyclization of the deprotected compound yields the desired compounds of general formula I. Any other suitable amino protecting group, such as e.g. Fmoc (9-fluorenylmethoxycarbonyl) or benzyloxycarbonyl (Z), can be alternatively used instead of the BOC group.

The deprotection-cyclization step can be carried out by treating the compounds of general formula III with for example a Bronsted acid such as trifluoroacetic acid (TFA) in an inert solvent such as dichloromethane (DCM). The reaction is preferably carried out at temperatures between 0° C. and 50° C. It may be advantageous to use also anisole or 1,3-dimethoxybenzene as a carbocation scavenger in the reaction mixture.

Compounds of general formula II, in which $R^1$, $R^2$ and X are as described above can be prepared according to scheme B, by reducing the nitro group in compounds of general formula VIa to the amino group. The reduction can for example be carried out using hydrogen gas in presence of a suitable catalyst like for example Raney-Nickel or Palladium on carbon. Another possible reduction method is using stannous(II)chloride ($SnCl_2.2H_2O$) in ethanol at temperatures between 70° C. and 80° C. (as described in Tetrahedron Lett. 25:839 (1984), or alternatively in polar aprotic solvents, like DMF, DMA or NMP and the like, optionally in the presence of bases, like for example pyridine or triethylamine and the like, at temperatures between 0° C. and 80° C. Another suitable method is using zinc-powder in the presence of ammonium chloride in protic solvents like, e.g., water or ethanol at temperatures between 20° C. and 80° C. The exact conditions for the respective compounds of general formula II can be found in the experimental part.

The protection of the amino function can be applied to a number of commercially available starting materials or compounds synthesized by anyone skilled in the art to produce the corresponding 2-nitroanilines with the general formula VI, in which X is a single bond and $R^1$ and $R^2$ are as described above.

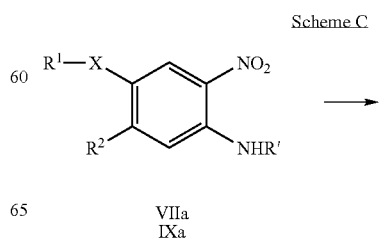

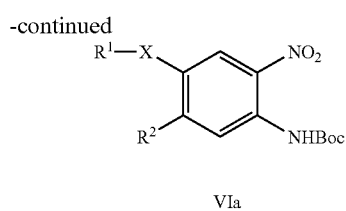

VIa wherein $R^2$ is Cl, F, OR" and R' is H in formula VIIa (general procedure, methods a, b or c below) and Ac in formula IXa (general procedure, method d below).

Reaction conditions are:
method a: diphosgene, EtOAc, 77° C.; then t-BuOH
method b: $Boc_2O$, $Cs_2CO_3$, 2-butanone, 52° C.
method c: i) $Boc_2O$, DMAP, THF; ii) TFA, DCM, 0° C.
method d: i) $Boc_2O$, DMAP, THF; ii) $NH_4OH$, THF As described in scheme C, compounds of the general formula VIa, in which $R^1$ is as described above, $R^2$ is chloro, fluoro or substituted oxygen and R' is hydrogen, can be prepared by protection of the amino group of compounds of the general formula VIIa, in which $R^1$ is as described above, $R^2$ is chloro, fluoro or substituted oxygen and R' is hydrogen, with a tert-butoxycarbonyl-group (BOC). One possibility for the protection of the amino function is for example reacting compounds of general formula VIIa with di-tert-butyl-carbonate in the presence of a base such as cesium carbonate. The reaction can be carried out in polar solvents such as acetone or butanone and the like at temperatures between 20° C. and 80° C.

Alternatively, the protection of the amino group can be achieved by preparing the intermediate isocyanate by treatment of compounds of the general formula VIIa, in which $R^1$ is as described above, $R^2$ is chloro, fluoro or substituted oxygen and R' is hydrogen, with diphosgene, preferably in aprotic solvents such as EtOAc or 1,4-dioxane at temperatures from 0° C. to 100° C., and subsequent treatment of the isocyanate with tert-butanol in solvents such as dichloromethane or 1,2-dichloroethane and the like at temperatures between 20° C. and 85° C. to give the desired compounds of general formula VIa.

Another suitable method to achieve this protection step is the intermediate formation of a di-BOC compound by treatment of compounds of the general formula VIIa, in which $R^1$ is as described above, $R^2$ is chloro, fluoro or substituted oxygen and R' is hydrogen, with di-tert-butyl-carbonate in the presence of DMAP in an aprotic solvent such as tetrahydrofuran and the like, followed by selective removal of a single BOC-group by treatment with a Bronsted-acid, like e.g. TFA, in aprotic solvents such as dichloromethane, chloroform or 1,2-dichloroethane at temperatures between 0° C. and 20° C. to give the desired compounds of general formula VIa.

Yet another suitable method to produce compounds of general formula XIa is the intermediate formation of a N—Ac—BOC compound by treatment of compounds of the general formula IXa, in which $R^1$ is as described above, $R^2$ is chloro or fluoro and R' is acetyl, with di-tert-butyl-carbonate in the presence of DMAP in an aprotic solvent such as tetrahydrofuran and the like, followed by selective removal of a single BOC-group by treatment with a Bronsted-base, like e.g. aqueous ammonia ($NH_4OH$), in aprotic solvents such as tetrahydrofuran, diethylether or 1,4-dioxane and the like, at temperatures between 0° C. and 20° C. to give the desired compounds of general formula VIa.

The protection of the amino function as shown in scheme C can be applied to a number of commercially available starting materials or compounds synthesized by standard transformations [e.g. nitration followed by selective ammonolysis of the halide in ortho-position to the newly introduced nitro-group as described in J. Med. Chem. 37:467 (1994); or ortho-nitration of acetanilide-compounds followed by deacetylation with for example. aqueous potassium hydroxide solution or aqueous hydrochloric acid as described in Org. Synth. 25:78 (1945) or in J. Med. Chem. 28:1387 (1985)] known to one skilled in the art to produce the corresponding 2-nitroanilines with the general formula VIIa, in which $R^1$ is as described above, $R^2$ is chloro br fluoro and R' is hydrogen, or 2-nitroacetanilides with the general formula IXa, in which $R^1$ is as described above, $R^2$ is chloro or fluoro and R' is acetyl. The exact conditions for the respective compounds used in this invention can be found in the experimental part.

Scheme D

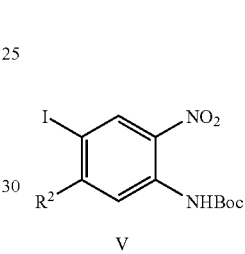

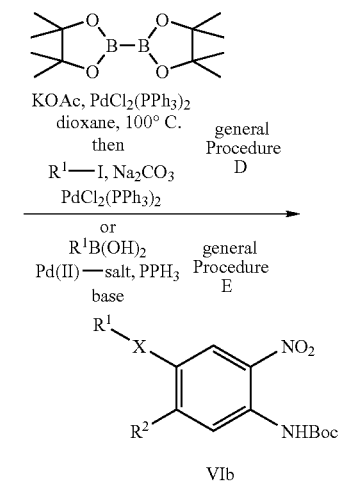

VIb

According to scheme D, compounds of general formula II in which $R^1$ is phenyl optionally substituted as described above for compounds where X is a single bond and $R^2$ is as described above, can be prepared by different routes depending on the nature of $R^1$ from the iodo-compounds of general formula V, in which $R^2$ is as described above. As shown in scheme D, the key step is a coupling reaction of Suzuki-type to produce compounds of the general formula VIb.

Compounds of general formula V, in which $R^2$ is as described above, can be prepared by different routes depending on the individual residue $R^2$. For example, a compound of formula V wherein $R^2$ is Cl, can be prepared from the commercially available 5-chloro-2-nitroaniline by iodination using iodine monochloride in acetic acid in the presence of sodium acetate at temperatures between 20° C. and 80° C. to give 5-chloro-4-iodo-2-nitroaniline, which in turn can be protected to yield a compound of formula V wherein $R^2$ is Cl.

According to scheme E, compounds of general formula VIb, in which $R^1$ is pyrrol-1-yl, X is a single bond and R is chloride, can be prepared from known 5-chloro-2-nitro-1,4-phenylenediamine [CAS-No. 26196-45-2] by selective condensation of the 4-amino-group with a suitable substituted 2,5-dimethoxy-tetrahydrofuran of the general formula VIII, as described in J. Heterocycl. Chem. 25:1003 (1988).

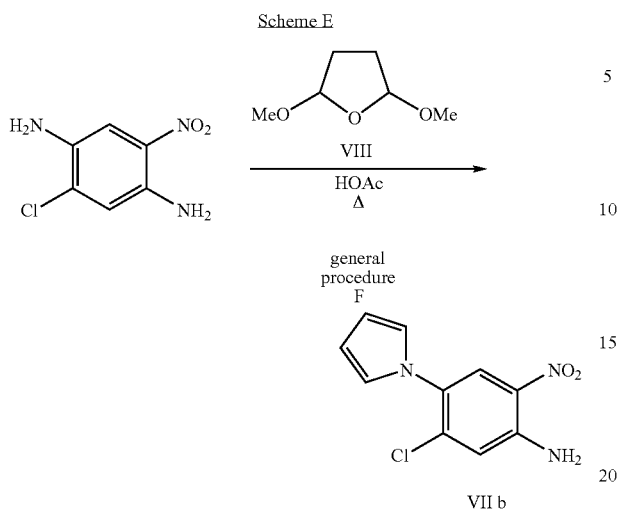

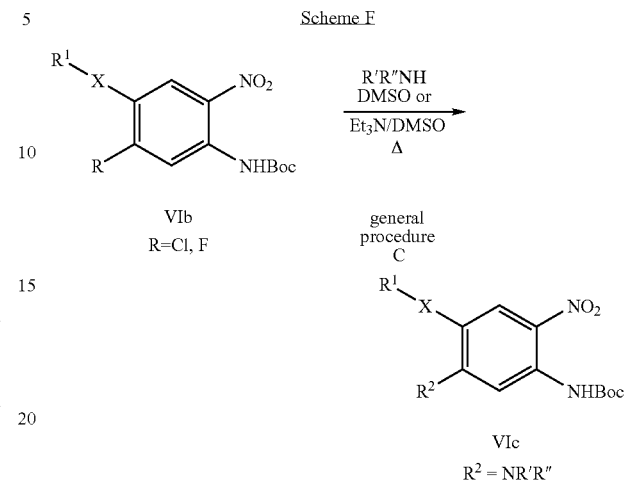

experimental part) by a nucleophilic substitution reaction with the respective amines in the presence of a suitable base.

The reaction is preferably carried out in acidic media, like for example acetic acid or propionic acid and the like, at temperatures between 40° C. to 100° C. The exact conditions for the respective compounds can be found in the experimental part.

As shown in scheme F, compounds of general formula VIc, in which $R^2$ is —NR'R", wherein R' and R" are hydrogen, $(C_1–C_7)$-alkyl or $C_3–C_7$-cycloalkyl, or:form a pyrrolidin-1-yl, piperidin-1-yl, or morpholine-4-yl, can be prepared from the intermediate compounds with the general formula VIc (which individual synthesis can be found in the The reaction is preferably carried out in a polar, aprotic solvent such as dimethyl formamide, N-methyl-pyrrolidone or dimethyl sulfoxide and the like. The base can be selected from the sterically hindered amines such as triethylamine or Hünig's base, alkoxides such as sodium methoxide and tert-butoxide, or hydrides such as sodium hydride. The reaction can be performed at temperatures between 20° C. and 110° C., depending on the individual compounds to be synthesized.

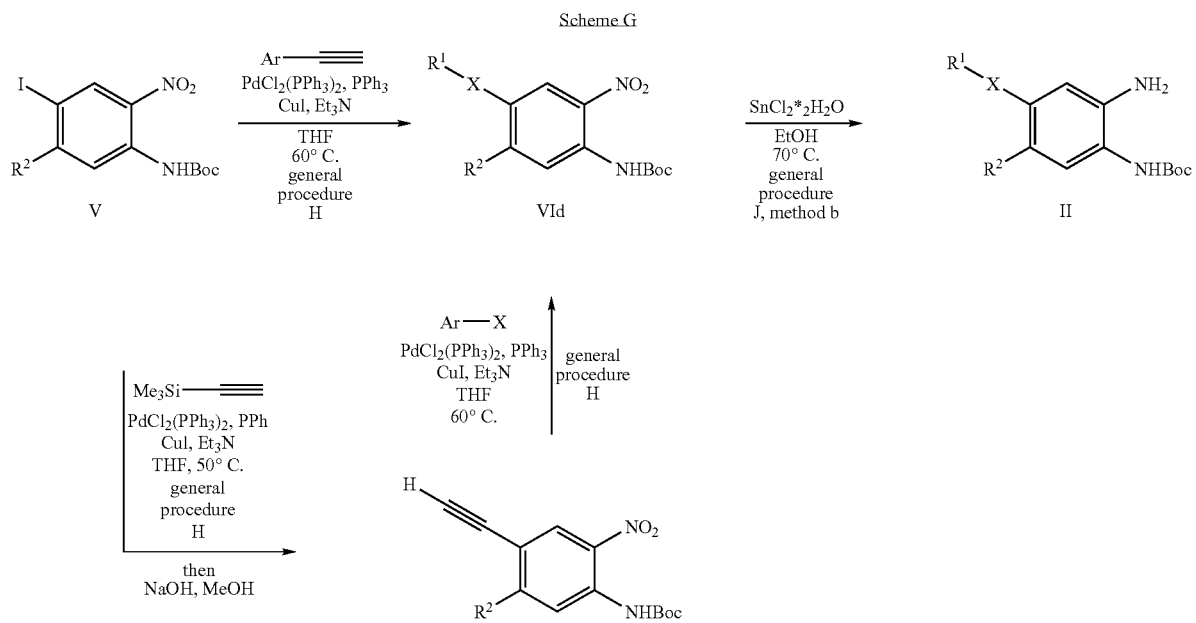

According to scheme G, compounds of general formula II in which R¹ is as described above for compounds where X is an ethynediyl group can be prepared by different routes from the iodo-compounds V, depending on the nature of R¹ and R². As shown in scheme F, the transformation can for example be carried out a) by directly attaching the R¹-alkynediyl-substituent to a compound of general formula V via a Sonogashira-type coupling to produce compounds of the general formula VId followed by the reduction of the nitro group, or
b) by two stepwise Sonogashira-type couplings, in which first trimethylsilyl-acetylene is coupled to a compound of general formula V to yield, after desilylation with sodium hydroxide in methanol, the intermediate X which then can be transformed via a second Sonogashira-type coupling with the appropriate reactant R¹—I, R¹—Br or R₁—OSO₂CF₃ into compounds of the general formula VId and reduction of the nitro group leads to the desired compounds of general formula II.

The exact conditions for the respective compounds can be found in the experimental part.

for example, hydrochloric acid, hydrobromic acid, sulfuric acid, nitric acid, phosphoric acid or citric acid, formic acid, fumaric acid, maleic acid, acetic acid, succinic acid, tartaric acid, methanesulfonic acid, p-toluenesulfonic acid and the like are suitable for the formation of pharmaceutically acceptable salts of basic compounds of formula I.

The present invention also provides a kit comprising:

a first compound being an AChE inhibitor and a pharmaceutically acceptable carrier, vehicle or diluent in a first unit dosage form;

a second compound being a mGluR2 antagonist; and a pharmaceutically acceptable carrier, vehicle or diluent in a second unit dosage form; and a container for containing said first and second unit dosage forms.

In another embodiment the present invention provides a kit comprising:

a first compound being an AChE inhibitor; and a pharmaceutically acceptable carrier, vehicle or diluent in a first unit dosage form;

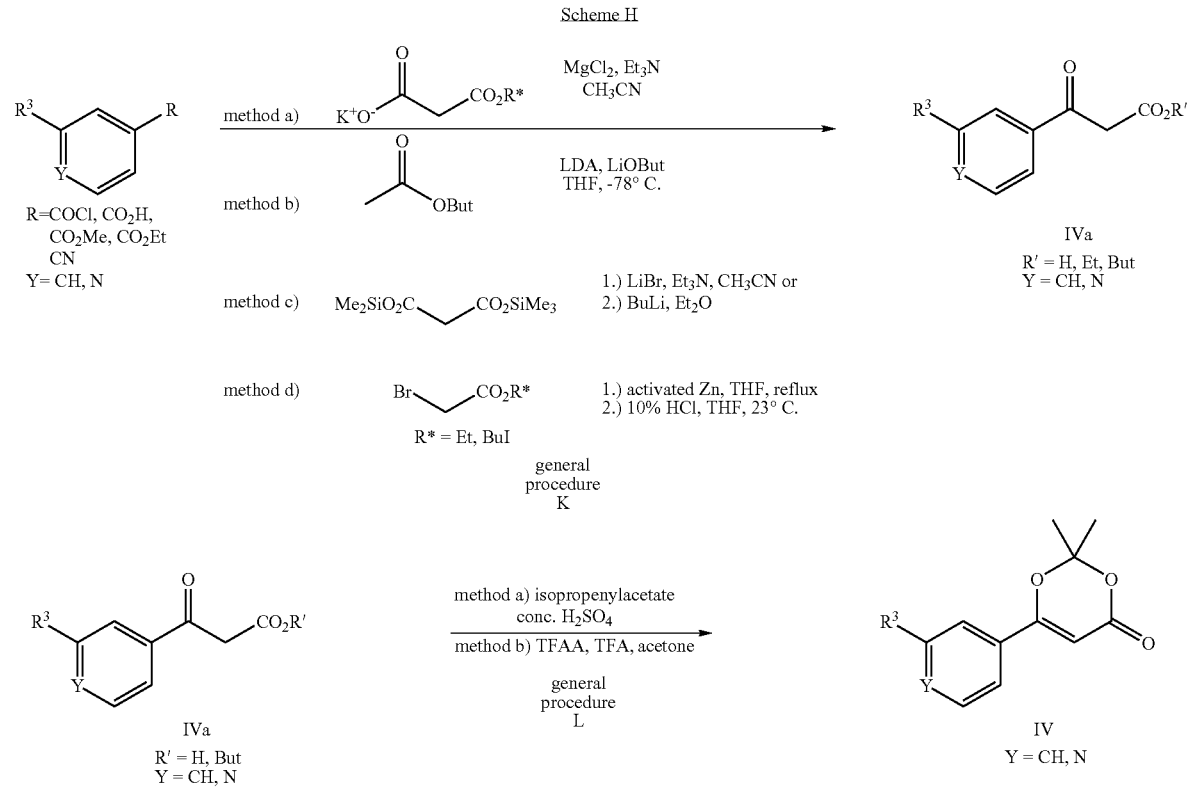

According to Scheme H, the dioxinones and β-keto esters building blocks with the general formula IV and IVa can be prepared by methods known to someone skilled in the art from the corresponding carboxylic acid derivatives R³—R, i.e. free acids, methyl or ethyl esters, acid chlorides and nitrites. The exact conditions for the corresponding compounds can be found in the experimental part.

The pharmaceutically acceptable addition salts can be manufactured readily according to methods known in the art and taking into consideration the nature of the compound to be converted into a salt. Inorganic or organic acids such as, a second compound being a dihydro-benzo[b][1,4]diazepin-2-one derivative or a prodrug thereof; and a pharmaceutically acceptable carrier, vehicle or diluent in a second unit dosage form; and a container for containing said first and second unit dosage forms.

In another embodiment the present invention provides a kit comprising:

a first compound being an AChE inhibitor; and a pharmaceutically acceptable carrier, vehicle or diluent in a first unit dosage form;

a second compound being a compound of formula I according to claim 3, a prodrug of said compound or isomer, or a pharmaceutically acceptable salt or solvate of said compound, isomer or prodrug; and a pharmaceutically acceptable carrier, vehicle or diluent in a second unit dosage form; and a container for containing said first and second unit dosage forms wherein the amounts of said first and second compounds result in an enhanced therapeutic effect, as described above.

The kit may further comprise a printed label or a set of printed instructions directing the use of the composition to treat a cognitive disorder.

The compositions of this invention may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. One or more active compounds may be present in association with one or more non-toxic pharmaceutically acceptable carriers and/or diluents and/or adjuvants and if desired other active ingredient. The compositions of the invention may be suitable for oral use, e.g., as tablets, troches, lozenges, aqueous or oily suspensions, dispersible powders or granules, emulsion, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredients in admixture with non-toxic pharmaceutically acceptable excipients that are suitable for the manufacture of tablets. These excipients may be for example, inert diluents, such as calcium carbonate sodium carbonate lactose, calcium phosphate or sodium phosphate; granulating and disintegrating agents, for example corn starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil. Aqueous suspensions contain the active materials in admixture with excipients suitable for the manufacture of aqueous suspensions. Such excipients are suspending agents, e.g., sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, e.g., lecithin, or condensation products of an alkylene oxide with fatty acids, e.g., polyoxythylene stearate, or condensation products of ethylene oxide with long chain aliphatic alcohols, e.g., heptadecaethyleneoxycetanol, or condensation products of ethylene oxide with partial esters derived from fatty acids and a hexitol such as polyoxyphenylene sorbitol monooleate. The aqueous suspension may also contain one or more preservatives, e.g., ethyl, or n-propyl p-hydroxybenzoate, one or more colouring agents, one or more flavouring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispensing or wetting agents and suspending agents are exemplified by those already mentioned above. Additional excipients, e.g., sweetening, flavoring and coloring agents, may also be present. The compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phospha-tides, for example soy bean, lecithin and esters or partial esters derived from fatty acids and hexitol, anhydrides, for example sorbitan monooleate, and condensation products of the said partial esters with ethylene oxide, for example polyoxyethylene sorbitan monooleate.

The emulsions may also contain sweetening and flavoring agents.

Syrups and elixirs may be formulated with sweetening agents, e.g., glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The composition of this invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug.

Such materials are cocoa butter and polyethylene glycols.

Active compounds may be administered parenterally in a sterile medium. The drug, depending on the vehicle and concentration used, can either be suspended or dissolved in the vehicle. Advantageously, adjuvants such as local anestetics, preservatives and buffering agents can be dissolved in the vehicle.

The total dosage of the mGluR2 antagonist and the AChE inhibitor in the combination is generally lower than the sum of the individual dosages normally administered and may, e.g. be in the range of from 0.01 to 10 mg/kg/day, or in the range of from 0.01 to 5 mg/kg/day, or in the range of from 0.01 to 2 mg/kg/day.

EXAMPLES

The compounds of formula I and their intermediates may be prepared according to the following procedures:

General procedure A: Preparation of (2-nitro-phenyl)-carbamic acid tert-butyl esters from 2-nitroanilines or 2-nitroacetanilides Method a (from 2-nitroanilines): To a solution of diphosgene (4.1 mL, 34.1 mmol) in EtOAc (40 mL) at 0° C. was added a solution of the 2-nitroaniline (45.5 mmol) in EtOAc (200–500 mL), and the mixture was heated to reflux for 18 h. The solvent was removed in vacuum to leave a brown solid, which was triturated with hot hexane (200 mL). The solid material was filtered off and the filtrate was concentrated under reduced pressure to leave the pure 2-nitrophenylisocyanate as a yellow solid. This material was refluxed in a mixture of excess tert-BuOH in $CH_2Cl_2$ for 2.5 h. Removal of the solvent left an orange solid which was purified by silica gel column chromatography with hexane/EtOAc to give the (2-nitro-phenyl)-carbamic acid tert-butyl ester as a yellow solid.

Method b (from 2-nitroanilines): To a mixture of the 2-nitroaniline (142 mmol) and cesium carbonate (55.5 g, 170 mmol) in 2-butanone (740 mL) was dropwise added a solution of $Boc_2O$ (37.8 g, 173 mmol) in 2-butanone (170 mL) and the resulting mixture was stirred at 50° C. to 80° C. until tlc indicated complete conversion. The solvent was removed in vacuum, the residue was treated with a mixture of $H_2O$ (240 mL) and MeOH (240 mL) and extracted with hexane (3×500 mL). The combined hexane layer was washed with brine (200 mL) and all aqueous layers were reextracted with hexane (300 mL). All combined hexane layers were dried over $MgSO_4$, filtered and the solvent was removed in vacuum to give an orange solid, which was purified by silica gel column chromatography with hexane/EtOAc to give the (2-nitro-phenyl)-carbamic acid tert-butyl ester as a yellow solid.

Method c (from 2-nitroanilines): To a solution of the 2-nitroaniline (550 mmol) and DMAP (1.22 g, 10 mmol) in THF (1000 mL) at 23° C. was dropwise added within 70 min a solution of $Boc_2O$ (246 g, 1128 mmol) in THF (500 mL) and stirring was continued at 23° C. for 75 min. The entire mixture was evaporated to dryness and dried at HV to leave a dark brown solid. This material was dissolved in DCM (1100 mL), cooled to 0° C. and TFA (84 mL, 1100 mmol) was added dropwise. The mixture was stirred at 0° C. for 2 h, poured into ice cold sat. $NaHCO_3$-solution, extracted with DCM, washed with brine and dried over $MgSO_4$. Removal of the solvent in vacuum left a dark brown solid which was coated on silica gel and purified by silica gel column chromatography with hexane/EtOAc to give the (2-nitro-phenyl)-carbamic acid tert-butyl ester as a yellow solid.

Method d (from 2-nitroacetanilides): To a solution of the 2-nitroacetanilide (100 mmol) and DMAP (122 mg, 1 mmol) in THF (100 mL) at 23° C. was dropwise added within 15 min a solution of $Boc_2O$ (22.92 g, 105 mmol) in THF (100 mL) and stirring was continued at 23° C. until tlc indicated completed conversion. The entire mixture was evaporated to dryness and dried at HV to leave a yellow to dark brown solid. This material was dissolved in THF (200 mL) and 25% $NH_4OH$ (77 mL, 500 mmol) was added dropwise. The mixture was stirred at 23° C. until tlc indicated complete conversion, poured into 1N HCl-solution, extracted with EtOAc, washed the organic layer with sat. $NaHCO_3$-solution and brine, dried over $MgSO_4$. Removal of the solvent in vacuum left a yellow to brown solid which was generally pure enough for further transformation or—if necessary—coated on silica gel and purified by silica gel column chromatography with hexane/EtOAc to give the (2-nitrophenyl)-carbamic acid tert-butyl ester as a yellow solid.

General procedure C: Preparation of 5-N-substituted-(2-nitro-phenyl)-carbamic acid tert-butyl esters (5-Chloro or -fluoro-2-nitro-phenyl)-carbamic acid tert-butyl ester was stirred with the desired amine optionally with DMSO, DMF, DMA, NMP or THF and/or DIPEA or $Et_3N$ at temperatures from 23° C. to 130° C. until tlc indicated complete disappearance of the chloride or fluoride. The reaction was cooled to 23° C. poured into ice-water, the precipitate was filtered off, washed with water and dried in vacuum. In cases were the product did not precipitate, the mixture was extracted with EtOAc, washed with water and brine, dried over $Na_2SO_4$. Filtration and removal of the solvent in vacuum left a crude product, which was—if necessary—purified by silica gel column chromatography with hexane/EtOAc to give the pure title compound.

General procedure F: Preparation of 2-nitro-4-pyrrol-1-yl-phenylamines by condensation of 2-nitro-1,4-phenylenediamine with 2,5-dimethoxytetrahydrofuran [cf. J. Heterocycl. Chem. 25:1003–1005 (1988)]

A mixture of the 2-nitro-1,4-phenylenediamine (25 mmol) and 2,5-dimethoxytetra-hydrofuran (26–32.5 mmol) in HOAc (150 mL) was stirred at 60–120° C. until tic indicated complete conversion of the phenylenediamine. After cooling to 23° C., the mixture was poured into brine (500 mL) and extracted with EtOAc (3×200 mL). The combined organic layers were washed with brine (300 mL) and dried over $MgSO_4$. Removal of the solvent left a brown residue, which was purified by silica gel column chromatography with cyclohexane/EtOAc to give the title compound.

General procedure J: Preparation of the (2-aminophenyl)-carbamic acid tert-butyl esters by reduction of (2-nitro-phenyl)-carbamic acid tert-butyl esters Method a: Catalytic hydrogenation: A mixture of the nitro compound (1.0 mmol) in MeOH or EtOH and THF (1:1 ca. 20 mL) [or solely EtOAc for aromatic chlorides] and 10% Palladium on carbon (20 mg), Raney-Ni (20 mg) or 5% Platinum on carbon was stirred vigorously at 23° C. under hydrogen atmosphere until tlc indicated complete conversion. The catalyst was filtered off, washed thoroughly with MeOH or EtOH and THF (1:1) [or EtOAc], the solvent was removed in vacuum to give the title compound, which was generally pure enough for further transformations, but could be crystallized from hot hexane or cyclohexane if necessary.

Method b: Reduction with $SnCl_2.2H_2O$: A mixture of the nitro compound (1.0 mmol) and $SnCl_2.2H_2O$ (5.0 mmol) was either stirred in EtOH (30 mL) at 70–80° C. or alternatively in pyridine (3 mL) and DMF (12 mL) at 23° C.

under Argon atmosphere until tlc indicated complete conversion [cf. Tetr. Lett. 25:839 (1984)]. The reaction mixture was brought to pH 8 by addition of sat. NaHCO$_3$-solution and extracted with EtOAc (2×100 mL). The combined organic layers were washed with brine and dried over Na$_2$SO$_4$. Removal of the solvent left a yellow solid, which—if necessary—can be purified by silica gel column chromatography.

Method c: Reduction with Zn and NH$_4$Cl: To a mixture of the nitro compound (1.0 mmol) in EtOH/THF/sat. NH$_4$Cl-solution (1:1:1, 30 mL) was added Zinc dust (3.0 mmol) and the mixture was stirred at 70° C. under Argon atmosphere until tlc indicated complete conversion. Aqueous workup as described in method b.

General Procedure K

Method a): Preparation of ethyl or tert-butyl 3-aryl-3-oxo-propionates: The ethyl or tert-butyl 3-aryl-3-oxo-propionates were prepared from the aryl acid chlorides and ethyl or tert-butyl malonate potassium salt [CAS-no. 6148-64-7 and 75486-33-8] with Et$_3$N and MgCl$_2$ in CH$_3$CN at 0° C. to 23° C. according to Synthesis 290 (1993). If the free aryl carboxylic acid was employed in this reaction, it was activated by treatment with ethyl chloroformate and Et$_3$N in THF/CH$_3$CN at 0° C. prior to reaction with the malonate salt.

Method b): Preparation of tert-butyl 3-aryl-3-oxo-propionates: The tert-butyl 3-aryl-3-oxo-propionates were alternatively prepared from the methyl or ethyl aryl esters by treatment with lithium tert-butyl acetate [prepared by treatment of tert-butyl acetate with lithium diisopropylamide in THF at −78° C.] in the presence of lithium tert-butoxide according to Synthesis 45 (1985). If the product contained residual starting material after workup, thus could be removed by selective saponification with LiOH in THF/MeOH/H$_2$O at 23° C.

Method c): Preparation of 3-aryl-3-oxo-propionic acids: The 3-aryl-3-oxo-propionic acids were prepared from the aryl acid chlorides and bis(trimethylsilyl)malonate with Et$_3$N and LiBr in CH$_3$CN at 0° C. according to Synth. Commun. 15:1039 (1985) (method c1) or with n-BuLi in ether at −60° C. to 0C. according to Synthesis 787 (1979) (method c2).

Method d): Preparation of ethyl or tert-butyl 3-aryl-3-oxo-propionates: The ethyl or tert-butyl 3-aryl-3-oxo-propionates were prepared from the aryl nitriles and ethyl or tert-butyl bromoacetate [CAS-No. 105-36-2 and 5292-43-3] with activated Zinc dust in THF at reflux, followed by treatment of the obtained enamino ester with 10% HCl in THF at 23° C. according to J. Org. Chem. 48:3835 (1983).

General procedure M: Preparation of {2-[3-aryl-3-oxo-propionylamino]-phenyl}-carbamic acid tert-butyl esters by reaction of (2-amino-phenyl)-carbamic acid tert-butyl esters with ethyl or tert-butyl 3-aryl-3-oxo-propionates or 6-aryl-2,2-dimethyl-[1,3]dioxin-4-ones A mixture of the (2-amino-phenyl)-carbamic acid tert-butyl ester or (1.0–1.2 mmol) and (1.0–1.5 mmol) of the ethyl or tert-butyl 3-aryl-3-oxo-propionate or 6-aryl-2,2-dimethyl-[1,3]dioxin-4-one was heated in toluene or xylene (4–8 mL) to 80° C. to 150° C. until tlc indicated complete consumption of the minor component. The solution was allowed to cool to 23° C., whereupon the product generally crystallized (in cases where crystallization failed to appear it was induced by addition of hexane or ether, alternatively the reaction mixture was directly subjected to silica gel column chromatography). The solid was filtered off, washed with ether or mixtures of ether/hexane and dried in vacuum to give the {2-[3-aryl-3-oxo-propionylamino]-phenyl}-carbamic acid tert-butyl esters, which was used directly in the following step or—if necessary—was purified by recrystallization or by silica gel column chromatography.

General procedure N: Preparation of 4-aryl-1,3-dihydro-benzo[b][1,4]diazepin-2-ones A solution or suspension of the {2-[3-aryl-3-oxo-propionylamino]-phenyl}-carbamic acid tert-butyl ester (1.0 mmol) in CH$_2$Cl$_2$ (5 mL) [anisole or 1,3-dimethoxybenzene (5–15 mmol) can be added if necessary] was treated with TFA (0.5–5.0 mL) at 0° C. and stirring was continued at 23° C. until tlc indicated complete consumption of the starting material.

Workup procedure a: The solvent was removed in vacuum, the residue treated with little ether, whereupon it crystallized. The solid was stirred with sat. NaHCO$_3$-solution or 1M Na$_2$CO$_3$-solution, filtered, washed with H$_2$O and ether or mixtures of ether/THF/MeOH and was dried to give the title compound, which if necessary can be purified by crystallization from 1,4-dioxane or by silica gel column chromatography with cyclohexane/EtOAc or EtOAc/EtOH.

Workup procedure b: The reaction mixture was diluted with DCM or EtOAc, washed with sat. NaHCO$_3$-solution or 1M Na$_2$CO$_3$-solution, brine and dried over MgSO$_4$ or Na$_2$SO$_4$. Removal of the solvent in vacuum left a material, which could be triturated with ether or mixtures of ether/THF/MeOH to give the title compound, or which if necessary can be purified by crystallization from 1,4-dioxane or by silica gel column chromatography with cyclohexane/EtOAc or EtOAc/EtOH.

In the following examples the following abbreviations were used: RT: room temperature; TFA: trifluoroacetic acid; TFAA: trifluoroacetic anhydride Example F1

2-Nitro-4-pyrrol-1-yl-phenylamine (Compound F1)

Compound F1 was prepared from 2-nitro-1,4-phenylenediamine [CAS-No. 5307-14-2) (20 g, 131 mmol) and 2,5-dimethoxytetrahydrofuran (18.3 mL, 135 mmol) in HOAc (37 ml) at 95° C. for 3 h according to the general procedure F.

Example A1

(5-Chloro-2-nitro-4-trifluoromethyl-phenyl)-carbamic acid tert-butyl ester (Compound A1)

Compound A1 was prepared via the di-Boc-compound from commercially available 5-chloro-2-nitro-4-trifluoromethyl-phenylamine [CAS-No. 35375-74-7](22.61 g, 94 mmol) and Boc$_2$O (42.06 g, 193 mmol), followed by treatment with 2 eq. TFA in CH$_2$Cl$_2$ according to the general procedure A (method c).

The following compounds were prepared in analogy to the method as described in Example A1:

| Compound name and number | Starting compound |
|---|---|
| (4-fluoro-2-nitro-phenyl)-carbamic acid tert-butyl ester (A2) | 4-fluoro-2-nitroaniline |
| (2-nitro-4-trifluoromethyl-phenyl)-carbamic acid tert-butyl ester (A3) | 4-amino-3-nitrobenzotrifluoride |
| (5-chloro-4-methyl-2-nitro-phenyl)-carbamic acid tert-butyl ester (A4) | 5-chloro-4-methyl-2-nitroaniline |

Example A5

(5-Fluoro-2-nitro-4-trifluoromethyl-phenyl)-carbamic acid tert-butyl ester (Compound A5)

Compound A5 was prepared via the di-Boc-compound from 5-fluoro-2-nitro-4-tri-fluoromethyl-phenylamine [which was prepared from commercially available 4-amino-2-fluorobenzotrifluoride by acetylation with Ac$_2$O in toluene at 23° C., followed by nitration with 100% nitric acid from 10–23° C. and deacetylation with 2N NaOH in THF at 50° C.] (5.21 g, 23.2 mmol) and Boc$_2$O (10.63 g, 48.7 mmol). After treatment with 2 eq. TFA in CH$_2$Cl$_2$ according to the general procedure A (method c) compound A5 was obtained.

Example A6

(4-Chloro-2-nitro-phenyl)-carbamic acid tert-butyl ester (Compound A6)

Compound A6 was prepared via the isocyanate from commercially available 4-chloro-2-nitro-phenylamine [CAS-No. 89-63-4] (5.0 g, 29 mmol) with diphosgene (1.75 mL, 14.5 mmol) in EtOAc (60 mL), followed by treatment with tert-BuOH (30 mL) in CH$_2$Cl$_2$ (60 mL) according to the general procedure A (method a).

Example A7

[2-Nitro-5-(2,2,2-trifluoro-ethoxy)-4-trifluoromethyl-phenyl]-carbamic acid tert-butyl ester (Compound A7)

Compound A7 was prepared via the di-Boc-compound from 2-nitro-5-(2,2,2-tri-fluoro-ethoxy)-4-trifluoromethyl-phenylamine [prepared by stirring commercially available 5-chloro-2-nitro-4-trifluoromethyl-phenylamine [CAS-No. 35375-74-7], 2,2,2-tri-fluoroethanol and KOH in DMSO at 23° C. for 32.5 days] and Boc$_2$O, followed by treatment with 2 eq. TFA in CH$_2$Cl$_2$ according to the general procedure A (method c).

Example A8

(5-Methoxy-2-nitro-4-trifluoromethyl-phenyl)-carbamic acid tert-butyl ester (Compound A8)

Compound A8 was prepared via the di-Boc-compound from 5-methoxy-2-nitro-4-trifluoromethyl-phenylamine [prepared by stirring commercially available 5-chloro-2-nitro-4-trifluoromethyl-phenylamine [CAS-No. 35375-74-7], methanol and KOH in DMSO at 23° C. for 10 days] (4.14 g, 17.5 mmol) and Boc$_2$O (8.04 g, 36.8 mmol), followed by treatment with 2 eq. TFA in CH$_2$Cl$_2$ according to the general procedure A (method c).

Example A9

(5-Ethoxy-2-nitro-4-trifluoromethyl-phenyl)-carbamic acid tert-butyl ester (Compound A9)

Compound A9 was prepared via the di-Boc-compound from 5-ethoxy-2-nitro-4-trifluoromethyl-phenylamine [prepared by stirring commercially available-5-chloro-2-nitro-4-trifluoromethyl-phenylamine [CAS-No. 35375-74-7], ethanol and KOH in DMSO at 60° C. for 7 days] (4.16 g, 16.6 mmol) and Boc$_2$O (7.62 g, 34.9 mmol), followed by treatment with 2 eq. TFA in CH$_2$Cl$_2$ according to the general procedure A (method c).

Example A10

(5-Methyl-2-nitro-4-trifluoromethyl-phenyl)-carbamic acid tert-butyl ester (Compound A10)

To a suspension of (5-chloro-2-nitro-4-trifluoromethyl-phenyl)-carbamic acid tert-butyl ester (Compound A1) (5.00 g, 14.7 mmol), tetrakis(triphenylphosphine)palladium (1.70 g, 1.47 mmol) and potassium carbonate (6.09 g, 44.1 mmol) in dioxane/water (9:1; 50 ml) was added at RT trimethylboroxine (2.04 ml, 14.7 mmol). The reaction mixture was stirred under reflux conditions for 15 h, filtered, evaporated and purified by column chromatography on silica gel (hexane/ethyl acetate 9:1) to yield compound A10.

Example A11:

(4-Methyl-2-nitro-5-trifluoromethyl-phenyl)-carbamic acid tert-butyl ester (Compound A11)

N-(4-Methyl-3-trifluoromethyl-phenyl)-acetamide Acetylation of commercially available 4-methyl-3-trifluoromethyl-aniline (10 g, 57.1 mmol) with acetic acid anhydride in toluene at RT gave N-(4-methyl-3-trifluoro-methyl-phenyl)-acetamide [CAS 22957-86-4].

b) N-(4-Methyl-2-nitro-5-trifluoromethyl-phenyl)-acetamide Nitration of N-(4-methyl-3-trifluoromethyl-phenyl)-acetamide (11.6 g, 53.5 mmol) in acetic acid anhydride gave a mixture of N-(4-methyl-2-nitro-5-trifluoromethyl-phenyl)-acetamide and N-(4-methyl-2-nitro-3-trifluoromethyl-phenyl)-acetamide. Separation of this mixture by column chromatography on silica gel (hexane/ethyl acetate 2:1) yielded N-(4-methyl-2-nitro-5-trifluoromethyl-phenyl)-acetamide (5.2 g, 37%).

c) (4-methyl-2-nitro-5-trifluoromethyl-phenyl)-carbamic acid tert-butyl ester Reaction of N-(4-methyl-2-nitro-5-trifluoromethyl-phenyl)-acetamide (5.0 g, 19.1 mmol) with Boc-anhydride (4.37 g, 20.0 mmol) according to the general procedure A (method d) and subsequent reaction with ammonium hydroxide (25%; 5.87 ml, 38.1 mmol) gave after aqueous work up and purification by column chromatography on silica gel (hexane/ethyl acetate 4:1) compound A11.

Example A12

(4-Chloro-2-nitro-5-trifluoromethyl-phenyl)-carbamic acid tert-butyl ester (Compound A12)

Reaction of N-(4-chloro-2-nitro-5-trifluoromethyl-phenyl)-acetamide [CAS 157554-77-3] (4.02 g, 14.2 mmol) with Boc-anhydride (3.26 g, 14.9 mmol) according to the general procedure A (method c) and subsequent reaction with ammonium hydroxide (25%; 4.38 ml, 28.4 mmol) gave after aqueous work up and purification by column chromatography on silica gel (hexane/ethyl acetate 4:1) compound A12.

Example A13

(2-Nitro-4-trifluoromethoxy-phenyl)-carbamic acid tert-butyl ester (Compound A13)

Reaction of commercially available N-(2-nitro-4-trifluoromethoxy-phenyl)-acetamide CAS-No.[787-57-5] (10.0 g, 37.6 mmol) with Boc-anhydride (8.68 g, 39.7 mmol) according to the general procedure A (method c) and subsequent reaction-with ammonium hydroxide (25%; 11.7 ml, 75.7 mmol). gave after aqueous work up and purification by column chromatography on silica gel (cyclohexane/ethyl acetate 4:1) compound A13.

Example A14

(5-Cyclopropylmethoxy-2-nitro-4-trifluoromethyl-phenyl)-carbamic acid tert-butyl ester (Compound A14)

Compound A14 was prepared via the di-Boc-compound from 5-cyclopropyl-meth-oxy-2-nitro-4-trifluoromethyl-phenylamine [prepared by stirring commercially available 5-chloro-2-nitro-4-trifluoromethyl-phenylamine [CAS-No. 35375-74-7], (hydroxy-methyl)cyclopropane and KOH in DMSO at 23° C. for 4 days and at 60° C. for 7 days] (4.49 g, 16.3 mmol) and Boc$_2$0 (7.45 g, 34.1 mmol), followed by treatment with 2 eq. TFA in CH$_2$Cl$_2$ according to the general procedure A (method c).

Example A15

(2-Nitro-4-trifluoromethyl-5-vinyl-phenyl)-carbamic acid tert-butyl ester (Compound A15)

A suspension of (5-chloro-2-nitro-4-trifluoromethyl-phenyl)-carbamic acid tert-butyl ester (Compound A1) (6.8 g, 20 mmol), vinyl boronic acid [CAS-No. 4363-34-2] {Bull. Soc. Chim. Fr. 8:2557–64 (1966)} (4.312 g, 60 mmol) and K$_2$CO$_3$ (8.29 g, 60 mmol) in water (10 mL) and dioxane (50 mL) was purged by Ar-stream at 23° C. for 10 min, then tetrakis(triphenylphosphine) palladium(0) (693 mg, 0.6 mmol) was added and the mixture was heated to 100° C. for 20 h, filtered, evaporated and purified by column chromatography on silica gel (hexane/ethyl acetate 9:1) to yield compound A15.

Example A16

(2-Nitro-4-pyrrol-1-yl-phenyl)-carbamic acid tert-butyl ester (Compound A16)

Compound A16 was prepared via the di-Boc-compound from 2-nitro-4-pyrrol-1-yl-phenylamine (F1) (13.5 g, 66.4 mmol) and Boc$_2$O (30.45 g, 139 mmol), followed by treatment with 2 eq. TFA in CH$_2$Cl$_2$ according to the general procedure A (method c).

Example C1

(5-Dimethylamino-2-nitro-4-trifluoromethyl-phenyl)-carbamic acid tert-butyl ester (Compound C1)

Compound C1 was prepared from (5-fluoro-2-nitro-4-trifluoromethyl-phenyl)-carbamic acid tert-butyl ester (A5) (1.62 g, 5.0 mmol) and dimethylamine (5.6 N in EtOH, 4.47 mL, 25.0 mmol) in DMSO (10 mL) at 23° C. according to the general procedure C.

Example J1

(2-Amino-4-chloro-phenyl)-carbamic acid tert-butyl ester (Compound J1)

Compound J1 was prepared from (4-chloro-2-nitro-phenyl)-carbamic acid tert-butyl ester (A6) (22.12 g, 85 mmol) by reduction with SnCl$_2$.2H$_2$O according to the general procedure J (method b).

The following compounds were prepared in analogy to the method as described above:

| Compound name and number | from |
|---|---|
| (2-amino-5-chloro-4-trifluoromethyl-phenyl)-carbamic acid tert-butyl ester (J2) | A1 |
| (2-amino-4-chloro-5-methyl-phenyl)-carbamic acid tert-butyl ester (J3) | A4 |
| (2-amino-4-chloro-5-trifluoromethyl-phenyl)-carbamic acid tert-butyl ester (J4) | A12 | from: starting compound

Example J5

(2-Amino-5-dimethylamino-4-trifluoromethyl-phenyl)-carbamic acid tert-butyl ester (Compound J5)

Compound J5 was prepared from (5-dimethylamino-2-nitro-4-trifluoromethyl-phenyl)-carbamic acid tert-butyl ester (C1) by hydrogenation with 10% Pd/C according to the general procedure J (method a).

The following compounds were prepared in analogy to the method as described above using an appropriate catalyst:

| Compound name and number | from |
|---|---|
| (2-amino-4-fluoro-phenyl)-carbamic acid tert-butyl ester (J6) | A2 |
| (2-amino-4-trifluoromethyl-phenyl)-carbamic acid tert-butyl ester (J7) | A3 |
| [2-amino-5-(2,2,2-trifluoro-ethoxy)-4-trifluoromethyl-phenyl]-carbamic acid tert-butyl ester (J8) | A7 |
| (2-amino-5-methoxy-4-trifluoromethyl-phenyl)-carbamic acid tert-butyl ester (J9) | A8 |
| (2-amino-5-ethoxy-4-trifluoromethyl-phenyl)-carbamic acid tert-butyl ester (J10) | A9 |
| (2-amino-5-methyl-4-trifluoromethyl-phenyl)-carbamic acid tert-butyl ester (J11) | A10 |
| (2-amino-4-methyl-5-trifluoromethyl-phenyl)-carbamic acid tert-butyl ester (J12) | A11 |
| (2-amino-4-trifluoromethoxy-phenyl)-carbamic acid tert-butyl ester (J13) | A13 |
| (2-amino-5-cyclopropylmethoxy-4-trifluoromethyl-phenyl)-carbamic acid tert-butyl ester (J14) | A14 |
| (2-amino-5-ethyl-4-trifluoromethyl-phenyl)-carbamic acid tert-butyl ester (J15) | A15 |
| (2-amino-4-pyrrol-1-yl-phenyl)-carbamic acid tert-butyl ester (J16) | A16 | from: starting compound

Example K1

3-Oxo-3-(3-pyridin-3-yl-phenyl)-propionic acid tert-butyl ester (Compound K1)

Compound K1 was prepared from 3-pyridin-3-yl-benzoic acid methyl ester [CAS-No. 79601-27-7] (1.00 g, 4.69 mmol) by treatment with lithium tert-butyl acetate according to general procedure K (method b).

3-oxo-3-(3-pyridin-4-yl-phenyl)-propionic acid tert-butyl ester (Compound K2) was prepared according to the method as described above, starting from 3-pyridin-4-yl-benzoic acid methyl ester.

Example K3

3-[3-(6-Methyl-pyridin-3-yl)-phenyl]-3-oxo-propionic acid tert-butyl ester (Compound K3)

Compound K3 was prepared from 3-(6-methyl-pyridin-3-yl)-benzoic acid methyl ester [prepared by the following procedure: A mixture of 3-carboxyphenylboronic acid (4.82 g, 29.07 mmol) and 3-bromo-2-methylpyridine (5.00 g, 29.07 mmol) in acetonitrile (145 mL) and 0.4M $Na_2CO_3$-solution (145 mL) was degassed and $Pd(Ph_3P)_4$ (1.68 g, 5 mol %) was added. The reaction mixture was refluxed for 16 h, evaporated to dryness (cf. Synlett 6:829–831 (2000). The residue was suspended in MeOH (400 mL) and $SOCl_2$ (10.5 mL, 145 mmol) was added dropwise at 23° C. and the reaction mixture was refluxed for 4 h. Evaporated to dryness, taken up in EtOAc, washed with sat. $NaHCO_3$-solution and brine, dried over $Na_2SO_4$. Removal of the solvent in vacuum left a brown oil, which was purified by silica gel column chromatography with cyclohexane/EtOAc.] (3.87 g, 17.0 mmol) by treatment with lithium tert-butyl acetate according to general procedure K (method b). Starting from 3-(2-methyl-pyridin-4-yl)-benzoic acid methyl ester, prepared in analogy to the method described above, 3-[3-(2-Methyl-pyridin-4-yl)-phenyl]-3-oxo-propionic acid tert-butyl ester (Compound K4) was prepared in analogy to the above method.

Example K5

3-[3-(2,6-Dimethyl-pyridin-4-yl)-phenyl]-3-oxo-propionic acid tert-butyl ester (Compound K5)

Compound K5 was obtained from 3-(2,6-dimethyl-pyridin-4-yl)-benzonitrile [prepared by the following procedure: A mixture of 3-cyanophenylboronic acid [CAS-No. 150255-96-2] (4.74 g, 32.25 mmol), 4-bromo-2,6-dimethylpyridine [Chem. Pharm. Bull. 38:2446 (1990) and J. Org. Chem. 27:1665 (1962)] (5.00 g, 26.87 mmol) and $K_3PO_4$ (8.56 g, 35.78 mmol) in dioxane (126 mL) was degassed and $Pd(Ph_3P)_4$ (1.53 g, 1.37 mmol) was added. The reaction mixture was stirred at 90° C. for 18 h. Evaporated to dryness, taken up in EtOAc, washed with sat. $NaHCO_3$-solution and brine, dried over $Na_2SO_4$. Removal of the solvent in vacuum left a brown solid, which was purified by silica gel column chromatography with cyclohexane/EtOAc.] (2.2 g, 10.6 mmol) by treatment with tert-butyl bromo-acetate and activated zinc, followed by hydrolysis with 10% HCl according to general procedure K (method d).

3-[3-(2-ethyl-pyridin-4-yl)-phenyl]-3-oxo-propionic acid tert-butyl ester (Compound K6) was prepared in analogy to the above method starting from 3-cyanophenylboronic acid and 4-bromo-2-ethyl-pyridine.

Example K7

3-[3-(6-Cyclopropyl-pyridin-3-yl)-phenyl]-3-oxo-propionic acid tert-butyl ester (Compound K7)

Compound K7 was obtained from 3-(6-cyclopropyl-pyridin-3-yl)-benzonitrile [prepared by the following procedure: A mixture of 3-cyanophenylboronic acid [CAS-No. 150255-96-2] (8.82 g, 60 mmol), crude 5-bromo-2-cyclopropylpyridine {prepared by the following procedure: A mixture of 2,5-dibromopyridine (11.85 g, 50 mmol), cyclopropyl zinc chloride (0.4 M in THF, 160 mL, 64 mmol), $Pd(PPh_3)_4$ (578 mg, 1 mol %) in THF (55 mL) was stirred under Argon atmosphere at 70° C. for 1.5 h. Cooled to RT, poured into sat. $NaHCO_3$-solution, extracted with ether, washed with brine, dried over $Na_2SO_4$. Removal of the solvent in vacuum left a brown oil (12.36 g).} (ca. 60 mmol), $Pd(PPh_3)_4$ (1.733 g, 3 mol %) and $K_2CO_3$ (13.82 g, 100 mmol) in toluene (250 mL), EtOH (22 mL) and $H_2O$ (50 mL) was stirred at 80° C. for 14 h. Cooled to RT, diluted with EtOAc, washed with sat. $NaHCO_3$-solution and brine, dried over $Na_2SO_4$. Removal of the solvent in vacuum left a brown solid, which was purified by silica gel column chromatography with cyclohexane/-EtOAc.] (9.88 g, 44.87 mmol) by treatment with tert-butyl bromoacetate and activated zinc, followed by hydrolysis with 10% HCl according to general procedure K (method d).

Example K8

3-[3-(2-Ethyl-6-methyl-pyridin-4-yl)-phenyl]-3-oxo-propionic acid tert-butyl ester (Compound K8)

Compound K8 was obtained from 3-(2-ethyl-6-methyl-pyridin-4-yl)-benzonitrile [prepared by the following procedure: A mixture of 3-cyanophenylboronic acid [CAS-No. 150255-96-2] (11.31 g, 76.9 mmol), 4-bromo-2-ethyl-6-methyl-pyridine [CAS-No. 155887-27-7] (12.83 g, 64.1 mmol), $Pd(PPh_3)_4$ (2.22 g, 3 mol %) and $K_2CO_3$ (17.73 g, 128.2 mmol) in toluene (360 mL), EtOH (29 mL) and $H_2O$ (72 mL) was stirred at 80° C. for 2 h. Cooled to RT, diluted with EtOAc, washed with sat. $NaHCO_3$-solution and brine, dried over $Na_2SO_4$. Removal of the solvent in vacuum left a brown solid, which was purified by silica gel column chromatography with cyclohexane/EtOAc.] (12.34 g, 55.5 mmol) by treatment with tert-butyl bromoacetate and activated zinc, followed by hydrolysis with 10% HCl according to general procedure K (method d).

Example K9

(RS)-3-Oxo-3-{3-[2-(tetrahydro-pyran-2-yloxymethyl)-pyridin-4-yl]-phenyl}-propionic acid tert-butyl ester (Compound K9)

Oxidation of 3-(2-methyl-pyridin-4-yl)-benzoic acid methyl ester (26.2 g, 0.11 mol; K4) with $H_2O_2$ (30%, 31.5 ml, 0.31 mol) in acetic acid (117 ml) at 70° C. for 27 h and subsequent reaction of the N-oxide in acetic acid anhydride (22 ml) at 135° C. for 30 min yielded after aqueous work-up 3-(2-acetoxymethyl-pyridin-4-yl)-benzoic acid methyl ester.

b) Hydrolysis of crude 3-(2-acetoxymethyl-pyridin-4-yl)-benzoic acid methyl ester (25.3 g, 0.09 mmol) with sodium methanolate (5.4M in methanol, 5 ml) in methanol (100 ml) at RT for 48 h led after aqueous work-up and purification by column chromatography (ethyl acetate) to 3-(2-hydroxymethyl-pyridin-4-yl)-benzoic acid methyl ester (brown oil, 14.7 g, 68%), which by reaction with 3,4-dihydro-2H-pyrane (9.3 ml, 0.10 mol) in dichloromethane (165 ml) at RT for 22h gave after aqueous work-up and purification by column chromatography (ethyl acetate) un-reacted material (9.46 g) and (RS)-3-[2-(tetrahydropyran-2-yloxymethyl)-pyridin-4-yl]-benzoic acid methyl ester.

c) Reaction of (RS)-3-[2-(tetrahydropyran-2-yloxymethyl)-pyridin-4-yl]-benzoic acid methyl ester with tert.- butyl acetate according to general procedure K (method d; example K15) yielded compound K9.

Example K10

3-[3-(6-Methyl-pyrimidin-4-yl)-phenyl]-3-oxo-propionic acid tert-butyl ester (Compound K10)

Compound K10 was prepared from 3-(6-methyl-pyrimidin-4-yl)-benzoic acid methyl ester [prepared by the following procedure: A solution of 3-chlorocarbonyl-benzoic acid methyl ester (19.9 g, 0.1 mol) in $Et_2O$ (20 ml) was added at 5° C. to a solution of 3-oxo-butyric acid tert-butyl ester magnesium salt [prepared from 3-oxo-butyric acid tert-butyl ester (13.4 ml, 82 mmol) and freshly prepared magnesium ethoxide [from Mg (2.65 g, 109 mol) in ethanol (25 ml)/CCl4 (0.5 ml)] according to Helv. Chim. Acta 35:2280 (1952)]. The mixture was stirred at RT for 15 h and then poured on sat. $NH_4Cl$-sol. The pH was set to 1.6 by the addition of 25% HCl and the mixture was extracted with $Et_2O$. The orange oil (27 g) obtained was heated in toluene (400 ml) in the presence of p-TsOH monohydrate (0.69 g, 3.6 mmol) to 100° C. for 4 h. After cooling, the solvent was evaporated in vacuum and the residue was dissolved in AcOEt. The solution was washed with sat. $NaHCO_3$-sol. and brine, dried over $Na_2SO_4$ and evaporated in vacuum to give 3-(3-oxo-butyryl)-benzoic acid methyl ester (15.6 g). A sample of this material (3.0 g, 13.6 mmol) was stirred with 2N KOH (40 ml) at RT for 10 min. The mixture was acidified to pH 1 with 3N HCl and the precipitate was isolated by filtration and triturated with AcOEt to give 3-(3-oxo-butyryl)-benzoic acid (2.3 g). A solution of this material (2.2 g, 11.0 mmol) in formamide (5.3 ml, 132 mmol) was heated to 180° C. for 1 h. The mixture was cooled and partitioned between AcOEt and sat. $NaHCO_3$-sol. The aqueous phase was acidified with 3N HCl to pH 2.6 and extracted with AcOEt and the crude product obtained was esterified by heating in MeOH (12 ml)/4N HCl-$Et_2O$ (3 ml) for 18 h at 40° C. to give the methyl ester as white crystals (0.33 g).] (0.8 g, 3.5 mmol) by treatment with lithium tert-butyl acetate according to general procedure K (method b).

Example K11

3-[2,3']Bipyridinyl-4-yl-3-oxo-propionic acid tert-butyl ester (Compound K11)

Compound K11 was prepared from [2,3']bipyridinyl-4-carboxylic acid methyl ester [prepared by the following procedure: A mixture of pyridine-3-boronic acid (0.7 g, 5.7 mmol), 2-bromo-isonicotinic acid (1.15 g, 5.7 mmol) and $K_2CO_3$ (0.63 g, 4.6 mmol) in $CH_3CN$ (120 mL)/$H_2O$ (10 mL) was degassed and $Pd(PPh_3)_4$ (0.13 g, 0.11 mmol) was added. The mixture was stirred for 24 h at 80° C. in an atmosphere of nitrogen and then concentrated in vacuum to a volume of ca. 10 ml. The pH was set to 6.by addition of 3N HCl and the solution was then evaporated in vacuum to dryness. The residue was stirred in 1N HCl-MeOH (23 ml) for 65 h at 50° C. The crude product was purified by chromatography (silica gel, AcOEt/cyclohexane 1:1) to give the methyl ester as light yellow oil (0.37 g).] (044 g, 2.1 mmol) by treatment with lithium tert-butyl acetate according to general procedure K (method b).

Example K12

3-(2'-Methyl-[2,4']bipyridinyl-4-yl)-3-oxo-propionic acid tert-butyl ester (Compound K12)

Compound K12 was prepared from 2'-methyl-[2,4']bipyridinyl-4-carboxylic acid methyl ester [prepared by the following procedure: A cooled solution of 4-bromo-2-methyl-pyridine (2.75 g) in $Et_2O$ (26 ml) was added at −78° C. over to a solution of 1.6 M butyl lithium/hexane (12 ml) in $Et_2O$ (50 ml). The solution was stirred for 20 min at −78° C. Triisopropylborate (4.8 ml, 20.8 mmol) was added and the mixture was allowed to warm up to RT over 1 hour and subsequently stirred for 18 h. $H_2O$ (13 ml) was added and the layers were separated. The organic layer was extracted with 0.5N NaOH (25 ml) and the combined aqueous layers were acidified to pH 6 with 2N HCl and then extracted with AcOEt (200 ml). The organic extract was dried and evaporated in vacuum and the residue was triturated with $Et_2O$ to give pyridine-2-methyl-4-boronic acid (0.36 g). A mixture of this material (0.36 g, 2.6 mmol), 2-bromo-isonicotinic acid (0.53 g, 2.6 mmol) and $K_2CO_3$ (0.29 g, 2.1 mmol) in $CH_3CN$ (9 ml)/$H_2O$ (4.5 ml) was degassed and $Pd(PPh_3)_4$ (0.12 g, 0.1 mmol) was added. The mixture was stirred for 70 h at 80° C. in an atmosphere of nitrogen and then concentrated in vacuum to a volume of ca. 5 ml. The pH was set to 6 by addition of 3N HCl and the solution was then evaporated to dryness in vacuum. The residue was stirred in 1N HCl-MeOH (30 ml) for 20 h at 50° C. The crude product was purified by chromatography (silica gel, AcOEt/cyclohexane 1:1) to give the methyl ester as light yellow oil (0.22 g).] (0.16 g, 0.71 mmol) by treatment with lithium tert-butyl acetate according to general procedure K (method b).

Example M1

{5-Dimethylamino-2-[3-oxo-3-(3-pyridin-3-yl-phenyl)-propionylamino]-4-trifluoromethyl-phenyl}-carbamic acid tert-butyl ester (Compound M1)

Compound M1 was prepared from (2-amino-5-dimethylamino-4-trifluoromethyl-phenyl)-carbamic acid tert-butyl ester (J5) (262 mg, 0.75 mmol) and 3-oxo-3-(3-pyridin-3-yl-phenyl)-propionic acid tert-butyl ester (K1) (223 mg, 0.75 mmol) according to the general procedure M.

The following compounds were prepared in analogy to Example M1:

| Compound name and number | from |
|---|---|
| {5-dimethylamino-2-[3-oxo-3-(3-pyridin-4-yl-phenyl)-propionylamino]-4-trifluoromethyl-phenyl}-carbamic acid tert-butyl ester (M2) | J5 and K2 |
| {2-[3-oxo-3-(3-pyridin-4-yl-phenyl)-propionylamino]-4-trifluoromethyl-phenyl}-carbamic acid tert-butyl ester (M3) | J7 and K2 |
| {4-chloro-2-[3-oxo-3-(3-pyridin-4-yl-phenyl)-propionylamino]-phenyl}-carbamic acid tert-butyl ester (M4) | J1 and K2 |

-continued

| Compound name and number | from |
|---|---|
| {2-[3-oxo-3-(3-pyridin-3-yl-phenyl)-propionylamino]-4-trifluoromethyl-phenyl}-carbamic acid tert-butyl ester (M5) | J7 and K1 |
| [2-[3-oxo-3-(3-pyridin-3-yl-phenyl)-propionylamino]-5-(2,2,2-trifluoro-ethoxy)-4-trifluoromethyl-phenyl]-carbamic acid tert-butyl ester (M6) | J8 and K1 |
| {5-ethoxy-2-[3-oxo-3-(3-pyridin-4-yl-phenyl)-propionylamino]-4-trifluoromethyl-phenyl}-carbamic acid tert-butyl ester (M7) | J10 and K2 |
| (5-ethoxy-2-{3-[3-(2-methyl-pyridin-4-yl)-phenyl]-3-oxo-propionylamino}-4-trifluoromethyl-phenyl)-carbamic acid tert-butyl ester (M8) | J10 and K4 |
| {5-methyl-2-[3-oxo-3-(3-pyridin-4-yl-phenyl)-propionylamino]-4-trifluoromethyl-phenyl}-carbamic acid tert-butyl ester (M9) | J11 and K2 |
| {4-chloro-5-methyl-2-[3-oxo-3-(3-pyridin-4-yl-phenyl)-propionylamino]-phenyl}-carbamic acid tert-butyl ester (M10) | J3 and K2 |
| {5-chloro-2-[3-oxo-3-(3-pyridin-4-yl-phenyl)-propionylamino]-4-trifluoromethyl-phenyl}-carbamic acid tert-butyl ester (M11) | J2 and K2 |
| (2'-fluoro-3-{3-[3-(2-methyl-pyridin-4-yl)-phenyl]-3-oxo-propionylamino}-biphenyl-4-yl)-carbamic acid tert-butyl ester (M12) | J17 and K4 |
| (4-chloro-5-methyl-2-{3-[3-(2-methyl-pyridin-4-yl)-phenyl]-3-oxo-propionylamino}-phenyl)-carbamic acid tert-butyl ester (M13) | J3 and K4 |
| (5-methyl-2-{3-[3-(2-methyl-pyridin-4-yl)-phenyl]-3-oxo-propionylamino}-4-trifluoromethyl-phenyl)-carbamic acid tert-butyl ester (M14) | J11 and K4 |
| (2-{3-[3-(2-methyl-pyridin-4-yl)-phenyl]-3-oxo-propionylamino}-4-trifluoromethyl-phenyl)-carbamic acid tert-butyl ester (M15) | J7 and K4 |
| (4-methyl-2-{3-[3-(2-methyl-pyridin-4-yl)-phenyl]-3-oxo-propionylamino}-5-trifluoromethyl-phenyl)-carbamic acid tert-butyl ester (M16) | J12 and K4 |
| (4-fluoro-2-{3-[3-(2-methyl-pyridin-4-yl)-phenyl]-3-oxo-propionylamino}-phenyl)-carbamic acid tert-butyl ester (M17) | J2 and K4 |
| (4-chloro-2-{3-[3-(2-methyl-pyridin-4-yl)-phenyl]-3-oxo-propionylamino}-5-trifluoromethyl-phenyl)-carbamic acid tert-butyl ester (M18) | J4 and K4 |
| (4-chloro-2-{3-[3-(2,6-dimethyl-pyridin-4-yl)-phenyl]-5-methyl-3-oxo-propionylamino}-phenyl)-carbamic acid tert-butyl ester (M19) | J3 and K5 |
| (2-{3-[3-(2,6-dimethyl-pyridin-4-yl)-phenyl]-5-methyl-3-oxo-propionylamino}-4-trifluoromethyl-phenyl)-carbamic acid tert-butyl ester (M20) | J11 and K5 |
| (2-{3-[3-(2,6-dimethyl-pyridin-4-yl)-phenyl]-3-oxo-propionylamino}-4-trifluoromethyl-phenyl)-carbamic acid tert-butyl ester (M21) | J7 and K5 |
| (2-{3-[3-(2,6-dimethyl-pyridin-4-yl)-phenyl]-4-methyl-3-oxo-propionylamino}-5-trifluoromethyl-phenyl)-carbamic acid tert-butyl ester (M22) | J12 and K5 |
| (5-chloro-2-{3-[3-(2,6-dimethyl-pyridin-4-yl)-phenyl]-3-oxo-propionylamino}-4-trifluoromethyl-phenyl)-carbamic acid tert-butyl ester (M23) | J2 and K5 |
| [2-{3-[3-(2,6-dimethyl-pyridin-4-yl)-phenyl]-3-oxo-propionylamino}-5-(2,2,2-trifluoro-ethoxy)-4-trifluoromethyl-phenyl]-carbamic acid tert-butyl ester (M24) | J8 and K5 |
| 5-ethoxy-[2-{3-[3-(2,6-dimethyl-pyridin-4-yl)-phenyl]-3-oxo-propionylamino}-4-trifluoromethyl-phenyl]-carbamic acid tert-butyl ester (M25) | J10 and K5 |
| (2-{3-[3-(2-ethyl-pyridin-4-yl)-phenyl]-5-methyl-3-oxo-propionylamino}-4-trifluoromethyl-phenyl)-carbamic acid tert-butyl ester (M26) | J11 and K6 |
| (2-{3-[3-(6-cyclopropyl-pyridin-3-yl)-phenyl]-3-oxo-propionylamino}-4-trifluoromethyl-phenyl)-carbamic acid tert-butyl ester (M27) | J7 and K7 |
| {5-methyl-2-[3-oxo-3-(3-pyridin-3-yl-phenyl)-propionylamino]-4-trifluoromethyl-phenyl}-carbamic acid tert-butyl ester (M28) | J11 and K1 |
| {5-methoxy-2-[3-oxo-3-(3-pyridin-3-yl-phenyl)-propionylamino]-4-trifluoromethyl-phenyl}-carbamic acid tert-butyl ester (M29) | J9 and K1 |
| {5-ethoxy-2-[3-oxo-3-(3-pyridin-3-yl-phenyl)-propionylamino]-4-tri fluoromethyl-phenyl}-carbamic acid tert-butyl ester (M30) | J10 and K1 |
| (2-{3-[3-(2-methyl-pyridin-4-yl)-phenyl]-3-oxo-propionylamino}-4-trifluoromethoxy-phenyl)-carbamic acid tert-butyl ester (M31) | J13 and K4 |
| (5-cyclopropylmethoxy-2-{3-[3-(2-methyl-pyridin-4-yl)-phenyl]-3-oxo-propionylamino}-4-trifluoromethyl-phenyl)-carbamic acid tert-butyl ester (M32) | J14 and K4 |
| (5-ethyl-2-{3-[3-(2-methyl-pyridin-4-yl)-phenyl]-3-oxo-propionylamino}-4-trifluoromethyl-phenyl)-carbamic acid tert-butyl ester (M33) | J15 and K4 |
| (2-{3-[3-(2,6-dimethyl-pyridin-4-yl)-phenyl]-3-oxo-propionylamino}-5-ethyl-4-trifluoromethyl-phenyl)-carbamic acid tert-butyl ester (M34) | J15 and K5 |
| (2-{3-[3-(2-ethyl-6-methyl-pyridin-4-yl)-phenyl]-3-oxo-propionylamino}-5-methyl-4-trifluoromethyl-phenyl)-carbamic acid tert-butyl ester (M35) | J11 and K8 |
| (RS)-[5-methyl-2-(3-oxo-3-{3-[2-(tetrahydropyran-2-yloxymethyl)-pyridin-4-yl]-phenyl}-propionylamino)-4-trifluoromethyl-phenyl]-carbamic acid tert-butyl ester (M36) | J11 and K9 | from: starting compound
*Compound J17: (3-amino-2'-fluoro-biphenyl-4-yl)-carbamic acid tert-butyl ester

Example 1

7,8-Dichloro-4-(3-pyridin-3-yl-phenyl)-1,3-dihydro-benzo[b][1,4]di-azepin-2-one (Compound 1)

Compound 1 was prepared from 4,5-dichlorophenylene-diamine (Compound J18) (172 mg, 0.97 mmol) and 3-oxo-3-(3-pyridin-3-yl-phenyl)-propionic acid tert-butyl ester (K1) (289 mg, 0.97 mmol) by refluxing in xylene according to the general procedure M. Obtained as an off-white solid (310 mg). MS (ISP) 382.2 [(M+H)⁺], 384 [(M+2+H)⁺] and 386 [(M+4+H)⁺]; mp 241° C.

The following compounds were prepared in accordance with Example 1:

| Compound name and number | from | MS (ISP)/mp |
|---|---|---|
| 7,8-dichloro-4-[3-(2-methyl-pyridin-4-yl)-phenyl]-1,3-dihydro-benzo[b][1,4]diazepin-2-one (2) | J18 and K4 | 394.1 [(M − H)⁻] 221° C. |
| 7,8-dichloro-4-[3-(2,6-dimethyl-pyridin-4-yl)-phenyl]-1,3-dihydro-benzo[b][1,4]diazepin-2-one (3) | J18 and K5 | 410.3 [(M + H)⁺] 226° C. | from: starting compound

Example 4

7-Dimethylamino-4-(3-pyridin-3-yl-phenyl)-8-trifluoromethyl-1,3-di-hydro-benzo[b][1,4]diazepin-2-one (Compound 4)

Compound 4 was prepared from {5-dimethylamino-2-[3-oxo-3-(3-pyridin-3-yl-phenyl)-propionylamino]-4-trifluoromethyl-phenyl}-carbamic acid tert-butyl ester (M1) (306 mg, 0.56 mmol) by treatment with TFA in CH₂Cl₂ according to the general procedure N. Obtained as a yellow solid (162 mg). MS (ISP) 425.4 [(M+H)⁺]; mp 204° C.

In analogy to the above Example the following compounds were prepared starting from the corresponding compounds:

| Compound name and number | from | MS (ISP)/mp |
|---|---|---|
| 7-dimethylamino-4-(3-pyridin-4-yl-phenyl)-8-trifluoromethyl-1,3-dihydro-benzo[b][1,4]diazepin-2-one (5) | M2 | 425.4 [(M + H)⁺] 202° C. |
| 4-(3-pyridin-4-yl-phenyl)-8-trifluoromethyl-1,3-dihydro-benzo[b][1,4]diazepin-2-one (6) | M3 | 382 [(M + H)⁺] |
| 8-chloro-4-(3-pyridin-4-yl-phenyl)-1,3-dihydro-benzo[b][1,4]diazepin-2-one (7) | M4 | 348 [(M + H)⁺] 350 [(M + 2 + H)⁺] 225–226° C. |
| 4-(3-pyridin-3-yl-phenyl)-8-trifluoromethyl-1,3-dihydro-benzo[b][1,4]diazepin-2-one (8) | M5 | 382 [(M + H)⁺] 216° C. |
| 4-(3-pyridin-3-yl-phenyl)-7-(2,2,2-trifluoro-ethoxy)-8-trifluoromethyl-1,3-dihydro-benzo[b][1,4]diazepin-2-one (9) | M6 | 480 [(M + H)⁺] mp 217° C. |
| 7-ethoxy-4-(3-pyridin-4-yl-phenyl)-8-trifluoromethyl-1,3-dihydro-benzo[b][1,4]diazepin-2-one (10) | M7 | 426.4 [(M + H)⁺] 206–207° C. (dec.) |
| 7-ethoxy-4-[3-(2-methyl-pyridin-4-yl)-phenyl]-8-trifluoromethyl-1,3-dihydro-benzo[b][1,4]diazepin-2-one (11) | M8 | 440 [(M + H)⁺] 236° C. |
| 7-methyl-4-(3-pyridin-4-yl-phenyl)-8-trifluoromethyl-1,3-dihydro-benzo[b][1,4]diazepin-2-one (12) | M9 | 396.3 [(M + H)⁺] 229° C. |
| 8-chloro-7-methyl-4-(3-pyridin-4-yl-phenyl)-1,3-dihydro-benzo[b][1,4]diazepin-2-one (13) | M10 | 362.2 [(M + H)⁺] 242° C. |
| 7-chloro-4-(3-pyridin-4-yl-phenyl)-8-trifluoromethyl-1,3-dihydro-benzo[b][1,4]diazepin-2-one (14) | M11 | 414.1 [(M − H)⁻] 216° C. |
| 8-(2-fluoro-phenyl)-4-[3-(2-methyl-pyridin-4-yl)-phenyl]-1,3-dihydro-benzo[b][1,4]diazepin-2-one (15) | M12 | 420.2 [(M − H)⁻] 205° C. |
| 8-chloro-7-methyl-4-[3-(2-methyl-pyridin-4-yl)-phenyl]-1,3-dihydro-benzo[b][1,4]diazepin-2-one (16) | M13 | 376.4 [(M + H)⁺] 215° C. |
| 7-methyl-4-[3-(2-methyl-pyridin-4-yl)-phenyl]-8-trifluoromethyl-1,3-dihydro-benzo[b][1,4]diazepin-2-one (17) | M14 | 410.4 [(M + H)⁺] 229° C. |
| 4-[3-(2-methyl-pyridin-4-yl)-phenyl]-8-trifluoromethyl-1,3-dihydro benzo[b][1,4]diazepin-2-one (18) | M15 | 396.3 [(M + H)⁺] 208° C. |
| 8-methyl-4-[3-(2-methyl-pyridin-4-yl)-phenyl]-7-trifluoromethyl-1,3-dihydro-benzo[b][1,4]diazepin-2-one (19) | M16 | 410.4 [(M + H)⁺] 215° C. |
| 8-fluoro-4-[3-(2-methyl-pyridin-4-yl)-phenyl]-1,3-dihydro-benzo[b][1,4]diazepin-2-one (20) | M17 | 346.3 [(M + H)⁺] 200° C. |
| 8-chloro-4-[3-(2-methyl-pyridin-4-yl)-phenyl]-7-trifluoromethyl-1,3-dihydro benzo[b][1,4]diazepin-2-one (21) | M18 | 430.4 [(M + H)⁺] 201° C. |
| 8-chloro-4-[3-(2,6-dimethyl-pyridin-4-yl)-phenyl]-7-methyl-1,3-dihydro-benzo[b][1,4]diazepin-2-one (22) | M19 | 390.3 [(M + H)⁺] 226° C. |
| 4-[3-(2,6-dimethyl-pyridin-4-yl)-phenyl]-7-methyl-8-trifluoromethyl-1,3-dihydro-benzo[b][1,4]diazepin-2-one (23) | M20 | 424.4 [(M + H)⁺] 229° C. |
| 4-[3-(2,6-dimethyl-pyridin-4-yl)-phenyl]-8-trifluoromethyl-1,3-dihydro benzo[b][1,4]diazepin-2-one (24) | M21 | 410.4 [(M + H)⁺] 221° C. |
| 4-[3-(2,6-dimethyl-pyridin-4-yl)-phenyl]-8-methyl-7-trifluoromethyl-1,3-dihydro benzo[b][1,4]diazepin-2-one (25) | M22 | 424.5 [(M + H)⁺] 223° C. |
| 7-chloro-4-[3-(2,6-dimethyl-pyridin-4-yl)-phenyl]-8-trifluoromethyl-1,3-dihydro benzo[b][1,4]diazepin-2-one (26) | M23 | 444.3 [(M + H)⁺] 229° C. |

-continued

| Compound name and number | from | MS (ISP)/mp |
|---|---|---|
| 4-[3-(2,6-dimethyl-pyridin-4-yl)-phenyl]-7-(2,2,2-trifluoroethoxy)-8-trifluoromethyl-1,3-dihydro-benzo[b][1,4]diazepin-2-one (27) | M24 | 508.3 [(M + H)$^+$] 232° C. |
| 4-[3-(2,6-dimethyl-pyridin-4-yl)-phenyl]-7-ethoxy-8-trifluoromethyl-1,3-dihydro-benzo[b][1,4]diazepin-2-one (28) | M25 | 454.5 [(M + H)$^+$] 239° C. |
| 4-[3-(2-ethyl-pyridin-4-yl)-phenyl]-7-methyl-8-trifluoromethyl-1,3-dihydro benzo[b][1,4]diazepin-2-one (29) | M26 | 424.4 [(M + H)$^+$] 228° C. |
| 4-[3-(6-cyclopropyl-pyridin-3-yl)-phenyl]-8-trifluoromethyl-1,3-dihydro-benzo[b][1,4]diazepin-2-one (30) | M27 | 422.3 [(M + H)$^+$] 179–181° C. |
| 7-methyl-4-(3-pyridin-3-yl-phenyl)-8-trifluoromethyl-1,3-dihydro-benzo[b][1,4]diazepin-2-one (31) | M28 | 396.3 [(M + H)$^+$] 206–207° C. |
| 7-methoxy-4-(3-pyridin-3-yl-phenyl)-8-trifluoromethyl-1,3-dihydro-benzo[b][1,4]diazepin-2-one (32) | M29 | 412.3 [(M + H)$^+$] 209–211° C. |
| 7-ethoxy-4-(3-pyridin-3-yl-phenyl)-8-trifluoromethyl-1,3-dihydro-benzo[b][1,4]diazepin-2-one (33) | M30 | 426.4 [(M + H)$^+$] 219–224° C. |
| 4-[3-(2-methyl-pyridin-4-yl)-phenyl]-8-trifluoromethoxy-1,3-dihydro-benzo[b][1,4]diazepin-2-one (34) | M31 | 412 [(M + H)$^+$] 200° C. |
| 7-cyclopropylmethoxy-4-[3-(2-methyl-pyridin-4-yl)-phenyl]-8-trifluoromethyl-1,3-dihydro-benzo[b][1,4]diazepin-2-one (35) | M32 | 466 [(M + H)$^+$] 203° C. |
| 7-ethyl-4-[3-(2-methyl-pyridin-4-yl)-phenyl]-8-trifluoromethyl-1,3-dihydro-benzo[b][1,4]diazepin-2-one (36) | M33 | 424 [(M + H)$^+$] |
| 4-[3-(2,6-dimethyl-pyridin-4-yl)-phenyl]-7-ethyl-8-trifluoromethyl-1,3-dihydro-benzo[b][1,4]diazepin-2-one (37) | M34 | 438 [(M + H)$^+$] 231° C. |
| 4-[3-(2-ethyl-6-methyl-pyridin-4-yl)-phenyl]-7-methyl-8-trifluoromethyl-1,3-dihydro-benzo[b][1,4]diazepin-2-one (38) | M35 | 438 [(M + H)$^+$] 212° C. |
| 4-[3-(2-hydroxymethyl-pyridin-4-yl)-phenyl]-7-methyl-8-trifluoromethyl-1,3-dihydro benzo[b][1,4]diazepin-2-one (39) | M36 | 424.2 [(M − H)$^-$] 215° C. | from: starting compound

Example 40

4-[3-(6-Methyl-pyridin-3-yl)-phenyl]-8-pyrrol-1-yl-1,3-dihydro-benzo[b][1,4]diazepin-2-one (Compound 40)

Compound 40 was prepared from (2-amino-4-pyrrol-1-yl-phenyl)-carbamic acid tert-butyl ester (J16) (273 mg, 1 mmol) and 3-[3-(6-methyl-pyridin-3-yl)-phenyl]-3-oxo-propionic acid tert-butyl ester (K3) (311 mg, 1 mmol) according to the general procedure M and subsequent treatment of the crude product according to the general procedure N. Obtained as a yellow solid (195 mg). MS (ISP) 393.2 [(M+H)$^+$]; mp 213–214° C.

In analogy to the method described above the following compounds were prepared:

| Compound name and number | from | MS/mp |
|---|---|---|
| 4-[2,3']bipyridinyl-4-yl-7-methyl-8-trifluoromethyl-1,3-dihydro-benzo[b][1,4]diazepin-2-one (41) | J11 and K11 | (ISP) 397.2 [(M + H)$^+$] 218–220° C. |
| 7-methyl-4-(2'-methyl-[2,4']bipyridinyl-4-yl)-8-trifluoromethyl-1,3-dihydro-benzo[b][1,4]diazepin-2-one (42) | J11 and K12 | (ISN) 409.5 [(M − H)$^-$] 238–240° C. |
| 4-[3-(6-methyl-pyrimidin-4-yl)-phenyl]-8-trifluoromethyl-1,3-dihydro-benzo[b][1,4]diazepin-2-one (43) | J7 and K10 | (ISP) 397.3 [(M + H)$^+$] 219–220° C. | from: starting compound

In the method of the invention the following mGluR2 antagonist containing tablets and capsules may be administered to a mammal in need thereof:

Example I

Tablets

Tablets of the following composition are produced in a conventional manner:

| | mg/Tablet |
|---|---|
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

Example II

Tablets

Tablets of the following composition are produced in a conventional manner:

| | mg/Tablet |
|---|---|
| Active ingredient | 200 |
| Powdered lactose | 100 |
| White corn starch | 64 |
| Polyvinylpyrrolidone | 12 |
| Na carboxymethylstarch | 20 |
| Magnesium stearate | 4 |
| Tablet weight | 400 |

Example III

Capsules

Capsules of the following composition are produced:

|  | mg/Capsule |
| --- | --- |
| Active ingredient | 50 |
| Crystalline. lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

Example B1

Combination of a mGluR2 antagonist and an AChE inhibitor against a scopolamine-induced working memory deficit in the delayed match to position (DMTP) task in rats Male Lister Hooded rats (Harlan, Netherlands), start weight approximately 250 g, were trained to asymptotic performance in an operant delayed match to position (DMTP) task, modified from the procedure originally published by Dunnett, Psychopharmacology (Berl) 87:357–63 (1985) (Higgins et al., Europ. J. Neuroscience 15:1827–1840 (2002); Higgins et al., Europ. J. Neuroscience 15:911–922 (2002); Higgins et al., Neuropharmacology 44:324–241 (2003)]. All rats were housed in groups of four in holding rooms at controlled temperature (20–22° C.) with a 12 h light/dark cycle (lights on at 0600 h). Access to food was restricted so as to maintain 85–90% of free feeding body weight. Except for during testing, water was available ad libitum at all times. The rats were tested in Med Associates operant chambers, equipped with 2 retractable levers positioned 7.5 cm either side of a central food tray. A single stimulus light (cue light) was positioned above each lever. Aluminum barriers (5.5 cm chamber extension) were fitted within the chamber to separate each lever from the food magazine. The chambers were controlled by Kestrel software (Conclusive Solutions, Harlow, UK) operating on an IBM compatible PC.

Rats were initially trained to lever press for a food reward (45 mg Formula 'P' pellet, Noyes, N.H.) on a continuous reinforcement (CRF) schedule with each lever presented singly an equal number of times (total 96 trials). On acquiring this behaviour the animals were next trained to make a matching response. Each trial consisted of a single lever being inserted into the chamber and the illumination of the appropriate stimulus light (sample stage). The rat was required to press the sample lever, which then immediately retracted. A single nosepoke into the central food tray resulted in the presentation of both levers and stimulus lights. Pressing the lever previously presented at the sample stage resulted in the delivery of a single food reward (choice stage). If the animal pressed the other lever, it was recorded as an incorrect response and was unrewarded. An incorrect response, or a failure to respond to the sample or choice levers during the 20 s limited hold (i.e. an omission), resulted in a time out period of 30 s. The next trial was signalled by illumination of the house light for a 5 s period, after which the sample lever was extended. The number of such trials per session was 96.

Initially, the delay between the sample and choice stage was 1 s after the first magazine nose poke. Once the animals had learned the matching rule ($\geq 90\%$ correct), the delay period was increased to 1, 2 and 4 s (32 trials per delay), up to a final level of 1, 2, 4, 8, 16, 24s. Sixteen trials were run at each delay. Drug testing began once rats performed at asymptote at this final level, which typically is 8–10 weeks from the start of training. The parameters measured include % correct (total no. correct/(total no. correct+incorrect)× 100) both for the total session and for each delay interval. Percent correct responses at each delay interval were analysed using an analysis of variance (ANOVA) with repeated measures on Treatment and Delay. Total percent correct responses were analysed using an ANOVA with repeated measures on Treatment. Post hoc tests were conducted by Newman-Keuls test. Statistical significance was accepted at $P<0.05$.

The experiment was conducted using a repeated measures design with each animal receiving each treatment according to a counterbalanced design. Animals were run 5 days/week, with drug treatment on 2 test days per week, separated by at least 2 days. Compound 23 and donepezil hydrochloride (Aricept) were prepared in 0.3% Tween 80 (v/v) in saline solution (0.9% NaCl) and both were administered p.o. using an administration volume of 5 ml/kg. Scopolamine hydrobromide was dissolved in saline solution and was administered s.c. using an injection volume of 1 ml/kg. Subjects were treated with Compound 23 (1 mg/kg per os by gavage) 180 min prior to testing, followed 145 min later by donepezil hydrochloride (1 mg/kg per os by gavage) and 5 min later by scopolamine (0.06 mg/kg). Scopolamine induced a significant delay-dependent reduction in percent correct responses, and a significant reduction in total correct responses collapsed over the delay intervals. In the above test the combination of AChE inhibitor and mGluR2 antagonist produced a reversal of the scopolamine deficit.

What is claimed is:

1. A method of treating acute or chronic neurological disorders comprising administering to a mammal in need thereof a pharmaceutical composition comprising a therapeutically effective amount of an AChE inhibitor selected from the group consisting of donepezil, rivastigmine, metrifonate, galantamine, physostigmine, tacrine, fordine, phenserine, citicoline and ganstigmine and an mGluR2 antagonist of formula I

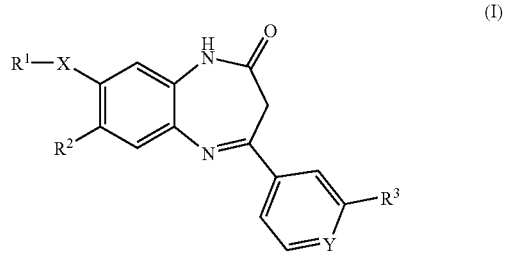

wherein

X is a single bond or an ethynediyl group;

Y is —CH= or =N—;

$R^1$ is, in case X is a single bond, selected from hydrogen, cyano, halogen, $(C_1-C_7)$-alkyl, $(C_1-C_7)$-alkoxy, fluoro-($C_1$–$C_7$)-alkyl, fluoro-($C_1$–$C_7$)-alkoxy, pyrrol-1-yl, unsubstituted phenyl, and phenyl substituted by one or two substituents selected from the group consisting of halogen, ($C_1$–$C_7$)-alkyl and fluoro-($C_1$–$C_7$)-alkyl; or $R^1$ is, in case X is an ethynediyl group, selected from unsubstituted phenyl, and phenyl substituted by one or two substituents selected from the group consisting of halogen, ($C_1$–$C_7$)-alkyl and fluoro-($C_1$–$C_7$)-alkyl;

$R^2$ is selected from hydrogen, ($C_1$–$C_7$)-alkyl, ($C_2$–$C_7$)-alkenyl, ($C_1$–$C_7$)-alkoxy, halogen, —NR'R", pyrrolidin-1-yl, piperidin-1-yl, morpholine-4-yl, fluoro-($C_1$–$C_7$)-alkyl, fluoro-($C_1$–$C_7$)-alkoxy, and ($C_1$–$C_7$)-alkoxy-(ethoxy)$_m$; wherein m is 1, 2, 3 or 4; and $R^3$ is a six-membered aromatic heterocycle ring containing 1 to 3 nitrogen atoms or a pyridine-N-oxide, which ring is unsubstituted or substituted by one or two substituents selected from the group consisting of halogen, fluoro-($C_1$–$C_7$)-alkyl, fluoro-($C_1$–$C_7$)-alkoxy, cyano, amino, ($C_1$–$C_7$)-alkylamino, ($C_1$–$C_7$)-dialkylamino, ($C_1$–$C_7$)-alkoxy-($C_1$–$C_7$)-alkylamino, ($C_1$–$C_7$)-hydroxy-($C_1$–$C_7$)-alkylamino, —($CH_2$)$_n$—C(O)—OR", —($CH_2$)$_n$—C(O)—NR'R", —($CH_2$)$_n$—$SO_2$—NR'R", —($CH_2$)$_n$—C($NH_2$)=NR", hydroxy, ($C_1$–$C_7$)-alkoxy, ($C_1$–$C_7$)-alkylthio, $C_3$–$C_7$-cycloalkyl, ($C_1$–$C_7$)-alkyl, and ($C_1$–$C_7$)-alkyl substituted by a group consisting of fluoro, —NR'R", hydroxy, ($C_1$–$C_7$)-alkoxy, pyrrolidin-1-yl, azetidin-1-yl, cyano and carbamoyloxy, wherein n is 0, 1, 2, 3 or 4; and R' and R" are each independently selected from hydrogen, ($C_1$–$C_7$)-alkyl and ($C_3$–$C_7$)-cycloalkyl;

or a pharmaceutically acceptable salt thereof.

2. The method according to claim 1 wherein the acute neurological disorder is Alzheimer's disease.

3. The method according to claim 1 wherein the chronic neurological disorder is mild cognitive impairment.

4. The method according to claim 1 wherein the AChE inhibitor and the mGluR2 antagonist are administered separately.

5. The method according to claim 4 wherein the AChE inhibitor and the mGluR2 antagonist are administered sequentially or simultaneously.

6. The method of claim 1 wherein the mGluR2 antagonist of formula I is selected from
   7-dimethylamino-4-(3-pyridin-3-yl-phenyl)-8-trifluoromethyl-1,3-dihydro-benzo-[b][1,4]diazepin-2-one,
   7-dimethylamino-4-(3-pyridin-4-yl-phenyl)-8-trifluoromethyl-1,3-dihydro-benzo-[b][1,4]diazepin-2-one,
   4-(3-pyridin-4-yl-phenyl)-8-trifluoromethyl-1,3-dihydro-benzo[b][1,4]diazepin-2-one,
   8-chloro-4-(3-pyridin-4-yl-phenyl)-1,3-dihydro-benzo[b][1,4]diazepin-2-one,
   4-(3-pyridin-3-yl-phenyl)-8-trifluoromethyl-1,3-dihydro-benzo[b][1,4]diazepin-2-one,
   4-(3-pyridin-3-yl-phenyl)-7-(2,2,2-trifluoro-ethoxy)-8-trifluoromethyl-1,3-dihydro-benzo[b][1,4]diazepin-2-one,
   7-ethoxy-4-(3-pyridin-4-yl-phenyl)-8-trifluoromethyl-1,3-dihydro-benzo[b][1,4]diazepin-2-one,
   7-ethoxy-4-[3-(2-methyl-pyridin-4-yl)-phenyl]-8-trifluoromethyl-1,3-dihydro-benzo-[b][1,4]diazepin-2-one,
   7-methyl-4-(3-pyridin-4-yl-phenyl)-8-trifluoromethyl-1,3-dihydro-benzo[b][1,4]diazepin-2-one, and
   8-chloro-7-methyl-4-(3-pyridin-4-yl-phenyl)-1,3-dihydro-benzo[b][1,4]diazepin-2-one.

7. The method of claim 1 wherein the mGluR2 antagonist of formula I is selected from
   7-chloro-4-(3-pyridin-4-yl-phenyl)-8-trifluoromethyl-1,3-dihydro-benzo[b][1,4]diazepin-2-one,
   7,8-dichloro-4-[3-(2-methyl-pyridin-4-yl)-phenyl]-1,3-dihydro-benzo[b][1,4]diazepin-2-one,
   8-(2-fluoro-phenyl)-4-[3-(2-methyl-pyridin-4-yl)-phenyl]-1,3-dihydro-benzo[b][1,4]diazepin-2-one,
   8-chloro-7-methyl-4-[3-(2-methyl-pyridin-4-yl)-phenyl]-1,3-dihydro-benzo[b][1,4]diazepin-2-one,
   7-methyl-4-[3-(2-methyl-pyridin-4-yl)-phenyl]-8-trifluoromethyl-1,3-dihydro-benzo-[b][1,4]diazepin-2-one,
   4-[3-(2-methyl-pyridin-4-yl)-phenyl]-8-trifluoromethyl-1,3-dihydro-benzo[b][1,4]diazepin-2-one,
   8-methyl-4-[3-(2-methyl-pyridin-4-yl)-phenyl]-7-trifluoromethyl-1,3-dihydro benzo-[b][1,4]diazepin-2-one,
   8-fluoro-4-[3-(2-methyl-pyridin-4-yl)-phenyl]-1,3-dihydro-benzo[b][1,4]diazepin-2-one,
   8-chloro-4-[3-(2-methyl-pyridin-4-yl)-phenyl]-7-trifluoromethyl-1,3-dihydro-benzo-[b][1,4]diazepin-2-one, and
   8-chloro-4-[3-(2,6-dimethyl-pyridin-4-yl)-phenyl]-7-methyl-1,3-dihydro-benzo[b][1,4]diazepin-2-one, and
   4-[3-(2,6-dimethyl-pyridin-4-yl)-phenyl]-7-methyl-8-trifluoromethyl-1,3-dihydro-benzo-[b][1,4]diazepin-2-one.

8. The method of claim 1 wherein the mGluR2 antagonist of formula I is selected from
   4-[3-(2,6-dimethyl-pyridin-4-yl)-phenyl]-8-trifluoromethyl-1,3-dihydro benzo[b][1,4]diazepin-2-one,
   4-[3-(2,6-dimethyl-pyridin-4-yl)-phenyl]-8-methyl-7-trifluoromethyl-1,3-dihydro-benzo-[b][1,4]diazepin-2-one,
   7-chloro-4-[3-(2,6-dimethyl-pyridin-4-yl)-phenyl]-8-trifluoromethyl-1,3-dihydro-benzo-[b][1,4]diazepin-2-one,
   7,8-dichloro-4-[3-(2,6-dimethyl-pyridin-4-yl)-phenyl]-1,3-dihydro-benzo[b][1,4]diazepin-2-one,
   4-[3-(2,6-dimethyl-pyridin-4-yl)-phenyl]-7-(2,2,2-trifluoro-ethoxy)-8-trifluoromethyl-1,3-dihydro-benzo[b][1,4]diazepin-2-one,
   4-[3-(2,6-dimethyl-pyridin-4-yl)-phenyl]-7-ethoxy-8-trifluoromethyl-1,3-dihydro-benzo-[b][1,4]diazepin-2-one,
   4-[3-(2-ethyl-pyridin-4-yl)-phenyl]-7-methyl-8-trifluoromethyl-1,3-dihydro-benzo-[b][1,4]diazepin-2-one,
   4-[3-(6-cyclopropyl-pyridin-3-yl)-phenyl]-8-trifluoromethyl-1,3-dihydro-benzo[b][1,4]diazepin-2-one,
   7-methyl-4-(3-pyridin-3-yl-phenyl)-8-trifluoromethyl-1,3-dihydro-benzo[b][1,4]diazepin-2-one, and
   7-methoxy-4-(3-pyridin-3-yl-phenyl)-8-trifluoromethyl-1,3-dihydro-benzo-[b][1,4]diazepin-2-one.

9. The method of claim 1 wherein the mGluR2 antagonist of formula I is selected from
   7-ethoxy-4-(3-pyridin-3-yl-phenyl)-8-trifluoromethyl-1,3-dihydro-benzo[b][1,4]diazepin-2-one,
   4-[3-(2-methyl-pyridin-4-yl)-phenyl]-8-trifluoromethoxy-1,3-dihydro-benzo[b][1,4]diazepin-2-one,
   7-cyclopropylmethoxy-4-[3-(2-methyl-pyridin-4-yl)-phenyl]-8-trifluoromethyl-1,3-dihydro-benzo[b][1,4]diazepin-2-one,
   7-ethyl-4-[3-(2-methyl-pyridin-4-yl)-phenyl]-8-trifluoromethyl-1,3-dihydro-benzo-[b][1,4]diazepin-2-one,
   4-[3-(2,6-dimethyl-pyridin-4-yl)-phenyl]-7-ethyl-8-trifluoromethyl-1,3-dihydro-benzo-[b][1,4]diazepin-2-one,
   4-[3-(2-ethyl-6-methyl-pyridin-4-yl)-phenyl]-7-methyl-8-trifluoromethyl-1,3-dihydro-benzo[b][1,4]diazepin-2-one, 4-[3-(2-hydroxymethyl-pyridin-4-yl)-phenyl]-7-methyl-8-trifluoromethyl-1,3-dihydro benzo[b][1,4]diazepin-2-one, 4-[2,3']bipyridinyl-4-yl-7-methyl-8-trifluoromethyl-1,3-dihydro-benzo[b][1,4]diazepin-2-one, 7-methyl-4-(2'-methyl-[2,4']bipyridinyl-4-yl)-8-trifluoromethyl-1,3-dihydro-benzo-[b][1,4]diazepin-2-one, and 4-[3-(6-methyl-pyrimidin-4-yl)-phenyl]-8-trifluoromethyl-1,3-dihydro-benzo[b][1,4]diazepin-2-one.

10. A pharmaceutical composition comprising an AChE inhibitor selected from the group consisting of donepezil, rivastigmine, metrifonate, galantamine, physostigmine, tacrine, fordine, phenserine, citicoline and ganstigmine and a mGluR2 antagonist of formula I

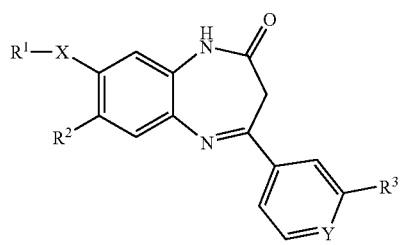

(I)

wherein
X is a single bond or an ethynediyl group;
Y is —CH= or =N—;
$R^1$ is, in case X is a single bond, selected from hydrogen, cyano, halogen, ($C_1$–$C_7$)-alkyl, ($C_1$–$C_7$)-alkoxy, fluoro-($C_1$–$C_7$)-alkyl, fluoro-($C_1$–$C_7$)-alkoxy, pyrrol-1-yl, unsubstituted phenyl, and phenyl substituted by one or two substituents selected from the group consisting of halogen, ($C_1$–$C_7$)-alkyl and fluoro-($C_1$–$C_7$)-alkyl; or
$R^1$ is, in case X is an ethynediyl group, selected from unsubstituted phenyl, and phenyl substituted by one or two substituents selected from the group consisting of alogen, ($C_1$–$C_7$)-alkyl and fluoro-($C_1$–$C_7$)-alkyl;
$R^2$ is selected from hydrogen, ($C_1$–$C_7$)-alkyl, ($C_2$–$C_7$)-alkenyl, ($C_1$–$C_7$)-alkoxy, halogen, —NR'R", pyrrolidin-1-yl, piperidin-1-yl, morpholine-4-yl, fluoro-($C_1$–$C_7$)-alkyl, fluoro-($C_1$–$C_7$)-alkoxy, and ($C_1$–$C_7$)-alkoxy-(ethoxy)$_m$; wherein m is 1, 2, 3 or 4; and
$R^3$ is a six-membered aromatic heterocycle ring containing 1 to 3 nitrogen atoms or a pyridine-N-oxide, which ring is unsubstituted or substituted by one or two substituents selected from the group consisting of halogen, fluoro-($C_1$–$C_7$)-alkyl, fluoro-($C_1$–$C_7$)-alkoxy, cyano, amino, ($C_1$–$C_7$)-alkylamino, ($C_1$–$C_7$)-dialkylamino, ($C_1$–$C_7$)-alkoxy-($C_1$–$C_7$)-alkylamino, ($C_1$–$C_7$)-hydroxy-($C_1$–$C_7$)-alkylamino, —($CH_2$)$_n$—C(O)—OR", —($CH_2$)$_n$—C(O)—NR'R", —($CH_2$)$_n$—SO$_2$—NR'R", —($CH_2$)$_n$—C($NH_2$)=NR", hydroxy, ($C_1$–$C_7$)-alkoxy, ($C_1$–$C_7$)-alkylthio, $C_3$–$C_7$-cycloalkyl, ($C_1$–$C_7$)-alkyl, and ($C_1$–$C_7$)-alkyl substituted by a group consisting of fluoro, —NR'R", hydroxy, ($C_1$–$C_7$)-alkoxy, pyrrolidin-1-yl, azetidin-1-yl, cyano and carbamoyloxy, wherein n is 0, 1, 2, 3 or 4; and
R' and R" are each independently selected from hydrogen, ($C_1$–$C_7$)-alkyl and ($C_3$–$C_7$)-cycloalkyl;

or a pharmaceutically acceptable addition salt thereof; and a pharmaceutically acceptable excipient.

11. The pharmaceutical composition of claim 10 wherein the mGluR2 antagonist of formula I is selected from 7-dimethylamino-4-(3-pyridin-3-yl-phenyl)-8-trifluoromethyl-1,3-dihydro-benzo-[b][1,4]diazepin-2-one, 7-dimethylamino-4-(3-pyridin-4-yl-phenyl)-8-trifluoromethyl-1,3-dihydro-benzo-[b][1,4]diazepin-2-one, 4-(3-pyridin-4-yl-phenyl)-8-trifluoromethyl-1,3-dihydro-benzo[b][1,4]diazepin-2-one, 8-chloro-4-(3-pyridin-4-yl-phenyl)-1,3-dihydro-benzo[b][1,4]diazepin-2-one, 4-(3-pyridin-3-yl-phenyl)-8-trifluoromethyl 1,3-dihydro-benzo[b][1,4]diazepin-2-one, 4-(3-pyridin-3-yl-phenyl)-7-(2,2,2-trifluoro-ethoxy)-8-trifluoromethyl-1,3-dihydro-benzo[b][1,4]diazepin-2-one, 7-ethoxy-4-(3-pyridin-4-yl-phenyl)-8-trifluoromethyl-1,3-dihydro-benzo[b][1,4]diazepin-2-one, 7-ethoxy-4-[3-(2-methyl-pyridin-4-yl)-phenyl]-8-trifluoromethyl-1,3-dihydro-benzo-[b][1,4]diazepin-2-one, 7-methyl-4-(3-pyridin-4-yl-phenyl)-8-trifluoromethyl-1,3-dihydro-benzo[b][1,4]diazepin-2-one, and 8-chloro-7-methyl-4-(3-pyridin-4-yl-phenyl)-1,3-dihydro-benzo[b][1,4]diazepin-2-one.

12. The pharmaceutical composition of claim 10 wherein the mGluR2 antagonist of formula I is selected from 7-chloro-4-(3-pyridin-4-yl-phenyl)-8-trifluoromethyl-1,3-dihydro-benzo[b][1,4]diazepin-2-one, 7,8-dichloro-4-[3-(2-methyl-pyridin-4-yl)-phenyl]-1,3-dihydro-benzo[b][1,4]diazepin-2-one, 8-(2-fluoro-phenyl)-4-[3-(2-methyl-pyridin-4-yl)-phenyl]-1,3-dihydro-benzo[b][1,4]diazepin-2-one, 8-chloro-7-methyl-4-[3-(2-methyl-pyridin-4-yl)-phenyl]-1,3-dihydro-benzo[b][1,4]diazepin-2-one, 7-methyl-4-[3-(2-methyl-pyridin-4-yl)-phenyl]-8-trifluoromethyl-1,3-dihydro-benzo-[b][1,4]diazepin-2-one, 4-[3-(2-methyl-pyridin-4-yl)-phenyl]-8-trifluoromethyl-1,3-dihydro-benzo[b][1,4]diazepin-2-one, 8-methyl-4-[3-(2-methyl-pyridin-4-yl)-phenyl]-7-trifluoromethyl-1,3-dihydro benzo-[b][1,4]diazepin-2-one, 8-fluoro-4-[3-(2-methyl-pyridin-4-yl)-phenyl]-1,3-dihydro-benzo[b][1,4]diazepin-2-one, 8-chloro-4-[3-(2-methyl-pyridin-4-yl)-phenyl]-7-trifluoromethyl-1,3-dihydro benzo-[b][1,4]diazepin-2-one, 8-chloro-4-[3-(2,6-dimethyl-pyridin-4-yl)-phenyl]-7-methyl-1,3-dihydro-benzo[b][1,4]diazepin-2-one, and 4-[3-(2,6-dimethyl-pyridin-4-yl)-phenyl]-7-methyl-8-trifluoromethyl-1,3-dihydro-benzo-[b][1,4]diazepin-2-one.

13. The pharmaceutical composition of claim 10 wherein the mGluR2 antagonist of formula I is selected from 4-[3-(2,6-dimethyl-pyridin-4-yl)-phenyl]-8-trifluoromethyl-1,3-dihydro benzo[b][1,4]diazepin-2-one, 4-[3-(2,6-dimethyl-pyridin-4-yl)-phenyl]-8-methyl-7-trifluoromethyl-1,3-dihydro-benzo-[b][1,4]diazepin-2-one, 7-chloro-4-[3-(2,6-dimethyl-pyridin-4-yl)-phenyl]-8-trifluoromethyl-1,3-dihydro-benzo-[b][1,4]diazepin-2-one, 7,8-dichloro-4-[3-(2,6-dimethyl-pyridin-4-yl)-phenyl]-1,3-dihydro-benzo[b][1,4]diazepin-2-one, 4-[3-(2,6-dimethyl-pyridin-4-yl)-phenyl]-7-(2,2,2-trifluoro-ethoxy)-8-trifluoromethyl-1,3-dihydro-benzo[b][1,4]diazepin-2-one, 4-[3-(2,6-dimethyl-pyridin-4-yl)-phenyl]-7-ethoxy-8-trifluoromethyl-1,3-dihydro-benzo-[b]1,4]diazepin-2-one, 4-[3-(2-ethyl-pyridin-4-yl)-phenyl]-7-methyl-8-trifluoromethyl-1,3-dihydro-benzo-[b][1,4]diazepin-2-one, 4-[3-(6-cyclopropyl-pyridin-3-yl)-phenyl]-8-trifluoromethyl-1,3-dihydro-benzo[b][1,4]diazepin-2-one, 7-methyl-4-(3-pyridin-3-yl-phenyl)-8-trifluoromethyl-1,3-dihydro-benzo[b][1,4]diazepin-2-one, and 7-methoxy-4-(3-pyridin-3-yl-phenyl)-8-trifluoromethyl-1,3-dihydro-benzo-[b][1,4]diazepin-2-one.

14. The pharmaceutical composition of claim 10 wherein the mGluR2 antagonist of formula I is selected from 7-ethoxy-4-(3-pyridin-3-yl-phenyl)-8-trifluoromethyl-1,3-dihydro-benzo[b][1,4]diazepin-2-one, 4-[3-(2-methyl-pyridin-4-yl)-phenyl]-8-trifluoromethoxy-1,3-dihydro-benzo[b][1,4]diazepin-2-one, 7-cyclopropylmethoxy-4-[3-(2-methyl-pyridin-4-yl)-phenyl]-8-trifluoromethyl-1,3-dihydro-benzo[b][1,4]diazepin-2-one, 7-ethyl-4-[3-(2-methyl-pyridin-4-yl)-phenyl]-8-trifluoromethyl-1,3-dihydro-benzo-[b][1,4]diazepin-2-one, 4-[3-(2,6-dimethyl-pyridin-4-yl)-phenyl]-7-ethyl-8-trifluoromethyl-1,3-dihydro-benzo-[b][1,4]diazepin-2-one, 4-[3-(2-ethyl-6-methyl-pyridin-4-yl)-phenyl]-7-methyl-8-trifluoromethyl-1,3-dihydro-benzo[b][1,4]diazepin-2-one, 4-[3-(2-hydroxymethyl-pyridin-4-yl)-phenyl]-7-methyl-8-trifluoromethyl-1,3-dihydro benzo[b][1,4]diazepin-2-one, 4-[2,3']bipyridinyl-4-yl-7-methyl-8-trifluoromethyl-1,3-dihydro-benzo[b][1,4]diazepin-2-one, 7-methyl-4-(2'-methyl-[2,4']bipyridinyl-4-yl)-8-trifluoromethyl-1,3-dihydro-benzo-[b][1,4]diazepin-2-one, and 4-[3-(6-methyl-pyrimidin-4-yl)-phenyl]-8-trifluoromethyl-1,3-dihydro-benzo[b][1,4diazepin-2-one.

15. A kit comprising:
a first unit dosage form comprising an AChE inhibitor selected from the group consisting of donepezil, rivastigmine, metrifonate, galantamine, physostigmine, tacrine, fordine, phenserine, citicoline and ganstigmine and a pharmaceutically acceptable excipient;
a second unit dosage form comprising a mGluR2 antagonist of formula I

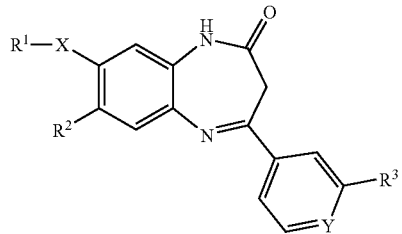

(I)

wherein
X is a single bond or an ethynediyl group;
Y is —CH═ or ═N—;
$R^1$ is, in case X is a single bond, selected from hydrogen, cyano, halogen, $(C_1-C_7)$-alkyl, $(C_1-C_7)$-alkoxy, fluoro-$(C_1-C_7)$-alkyl, fluoro-$(C_1-C_7)$-alkoxy, pyrrol-1-yl, unsubstituted phenyl, and phenyl substituted by one or two substituents selected from the group consisting of halogen, $(C_1-C_7)$-alkyl and fluoro-$(C_1-C_7)$-alkyl; or
$R^1$ is, in case X is an ethynediyl group, selected from unsubstituted phenyl, and phenyl substituted by one or two substituents selected from the group consisting of halogen, $(C_1-C_7)$-alkyl and fluoro-$(C_1-C_7)$-alkyl;
$R^2$ is selected from hydrogen, $(C_1-C_7)$-alkyl, $(C_2-C_7)$-alkenyl, $(C_1-C_7)$-alkoxy, halogen, —NR'R", pyrrolidin-1-yl, piperidin-1-yl, morpholine-4-yl, fluoro-$(C_1-C_7)$-alkyl, fluoro-$(C_1-C_7)$-alkoxy, and $(C_1-C_7)$-alkoxy-(ethoxy)$_m$; wherein m is 1, 2, 3 or 4; and
$R^3$ is a six-membered aromatic heterocycle ring containing 1 to 3 nitrogen atoms or a pyridine-N-oxide, which ring is unsubstituted or substituted by one or two substituents selected from the group consisting of halogen, fluoro-$(C_1-C_7)$-alkyl, fluoro-$(C_1-C_7)$-alkoxy, cyano, amino, $(C_1-C_7)$-alkylamino, $(C_1-C_7)$-dialkylamino, $(C_1-C_7)$-alkoxy-$(C_1-C_7)$-alkylamino, $(C_1-C_7)$-hydroxy-$(C_1-C_7)$-alkylamino, —$(CH_2)_n$—C(O)—OR", —$(CH_2)_n$—C(O)—NR'R", —$(CH_2)_n$—SO$_2$—NR'R", —$(CH_2)_n$—C(NH$_2$)═NR", hydroxy, $(C_1-C_7)$-alkoxy, $(C_1-C_7)$-alkylthio, $C_3-C_7$-cycloalkyl, $(C_1-C_7)$-alkyl, and $(C_1-C_7)$-alkyl substituted by a group consisting of fluoro, —NR'R", hydroxy, $(C_1-C_7)$-alkoxy, pyrrolidin-1-yl, azetidin-1-yl, cyano and carbamoyloxy, wherein n is 0, 1, 2, 3 or 4; and
R' and R" are each independently selected from hydrogen, $(C_1-C_7)$-alkyl and $(C_3-C_7)$-cycloalkyl;
or an isomer,
or a pharmaceutically acceptable salt thereof; and
a pharmaceutically acceptable excipient; and
a container for containing said first and second unit dosage forms.

16. The kit of claim 15 wherein the mGluR2 antagonist of formula I is selected from 7-dimethylamino-4-(3-pyridin-3-yl-phenyl)-8-trifluoromethyl-1,3-dihydro-benzo-[b][1,4]diazepin-2-one, 7-dimethylamino-4-(3-pyridin-4-yl-phenyl)-8-trifluoromethyl-1,3-dihydro-benzo-[b][1,4]diazepin-2-one, 4-(3-pyridin-4-yl-phenyl)-8-trifluoromethyl-1,3-dihydro-benzo[b][1,4]diazepin-2-one, 8-chloro-4-(3-pyridin-4-yl-phenyl)-1,3-dihydro-benzo[b][1,4]diazepin-2-one, 4-(3-pyridin-3-yl-phenyl)-8-trifluoromethyl-1,3-dihydro-benzo[b][1,4]diazepin-2-one, 4-(3-pyridin-3-yl-phenyl)-7-(2,2,2-trifluoro-ethoxy)-8-trifluoromethyl-1,3-dihydro-benzo[b][1,4]diazepin-2-one, 7-ethoxy-4-(3-pyridin-4-yl-phenyl)-8-trifluoromethyl-1,3-dihydro-benzo[b][1,4]diazepin-2-one, 7-ethoxy-4-[3-(2-methyl-pyridin-4-yl)-phenyl]-8-trifluoromethyl-1,3-dihydro-benzo-[b][1,4]diazepin-2-one, 7-methyl-4-(3-pyridin-4-yl-phenyl)-8-trifluoromethyl-1,3-dihydro-benzo[b][1,4]diazepin-2-one, and 8-chloro-7-methyl-4-(3-pyridin-4-yl-phenyl)-1,3-dihydro-benzo[b][1,4]diazepin-2-one.

17. The kit of claim 15 wherein the mGluR2 andtagonist of formula I is selected from 7-chloro-4-(3-pyridin-4-yl-phenyl)-8-trifluoromethyl-1,3-dihydro-benzo[b][1,4]diazepin-2-one, 7,8-dichloro-4-[3-(2-methyl-pyridin-4-yl)-phenyl]-1,3-dihydro-benzo[b][1,4]diazepin-2-one, 8-(2-fluoro-phenyl)-4-[3-(2-methyl-pyridin-4-yl)-phenyl]-1,3-dihydro-benzo[b][1,4]diazepin-2-one, 8-chloro-7-methyl-4-[3-(2-methyl-pyridin-4-yl)-phenyl]-1,3-dihydro-benzo[b][1,4]diazepin-2-one, 7-methyl-4-[3-(2-methyl-pyridin-4-yl)-phenyl]-8-trifluoromethyl-1,3-dihydro-benzo-[b][1,4]diazepin-2-one, 4-[3-(2-methyl-pyridin-4-yl)-phenyl]-8-trifluoromethyl-1,3-dihydro-benzo[b][1,4]diazepin-2-one, 8-methyl-4-[3-(2-methyl-pyridin-4-yl)-phenyl]-7-trifluoromethyl-1,3-dihydro benzo-[b][1,4]diazepin-2-one, 8-fluoro-4-[3-(2-methyl-pyridin-4-yl)-phenyl]-1,3-dihydro-benzo[b][1,4]diazepin-2-one, 8-chloro-4-[3-(2-methyl-pyridin-4-yl)-phenyl]-7-trifluoromethyl-1,3-dihydro benzo-[b][1,4]diazepin-2-one,
8-chloro-4-[3-(2,6-dimethyl-pyridin-4-yl)-phenyl]-7-methyl-1,3-dihydro-benzo[b][1,4]diazepin-2-one, and
4-[3-(2,6-dimethyl-pyridin-4-yl)-phenyl]-7-methyl-8-trifluoromethyl-1,3-dihydro-benzo-[b][1,4]diazepin-2-one.

18. The kit of claim 15 wherein the mGluR2 antagonist of formula I is selected from 4-[3-(2,6-dimethyl-pyridin-4-yl)-phenyl]-8-trifluoromethyl-1,3-dihydro benzo[b][1,4]diazepin-2-one,
4-[3-(2,6-dimethyl-pyridin-4-yl)-phenyl]-8-methyl-7-trifluoromethyl-1,3-dihydro-benzo-[b][1,4]diazepin-2-one,
7-chloro-4-[3-(2,6-dimethyl-pyridin-4-yl)-phenyl]-8-trifluoromethyl-1,3-dihydro-benzo-[b][1,4]diazepin-2-one,
7,8-dichloro-4-[3-(2,6-dimethyl-pyridin-4-yl)-phenyl]-1,3-dihydro-benzo[b][1,4]diazepin-2-one,
4-[3-(2,6-dimethyl-pyridin-4-yl)-phenyl]-7-(2,2,2-trifluoro-ethoxy)-8-trifluoromethyl-1,3]-dihydro-benzo[b][1,4]diazepin-2-one,
4-[3-(2,6-dimethyl-pyridin-4-yl)-phenyl]-7-ethoxy-8-trifluoromethyl-1,3-dihydro-benzo-[b][1,4]diazepin-2-one,
4-[3-(2-ethyl-pyridin-4-yl)-phenyl]-7-methyl-8-trifluoromethyl-1,3-dihydro-benzo-[b][1,4]diazepin-2-one,
4-[3-(6-cyclopropyl-pyridin-3-yl)-phenyl]-8-trifluoromethyl-1,3-dihydro-benzo[b][1,4]diazepin-2-one,
7-methyl-4-(3-pyridin-3-yl-phenyl)-8-trifluoromethyl-1,3-dihydro-benzo[b][1,4]diazepin-2-one, and
7-methoxy-4-(3-pyridin-3-yl-phenyl)-8-trifluoromethyl-1,3-dihydro-benzo-[b][1,4]diazepin-2-one.

19. The kit of claim 15 wherein the mGluR2 antagonist of formula I is selected from
7-ethoxy-4-(3-pyridin-3-yl-phenyl)-8-trifluoromethyl-1,3-dihydro-benzo[b][1,4]diazepin-2-one,
4-[3-(2-methyl-pyridin-4-yl)-phenyl]-8-trifluoromethoxy-1,3-dihydro-benzo[b][1,4]diazepin-2-one,
7-cyclopropylmethoxy-4-[3-(2-methyl-pyridin-4-yl)-phenyl]-8-trifluoromethyl-1,3-dihydro-benzo[b][1,4]diazepin-2-one,
7-ethyl-4-[3-(2-methyl-pyridin-4-yl)-phenyl]-8-trifluoromethyl-1,3-dihydro-benzo-[b][1,4]diazepin-2-one,
4-[3-(2,6-dimethyl-pyridin-4-yl)-phenyl]-7-ethyl-8-trifluoromethyl-1,3-dihydro-benzo-[b][1,4]diazepin-2-one,
4-[3-(2-ethyl-6-methyl-pyridin-4-yl)-phenyl]-7-methyl-8-trifluoromethyl-1,3-dihydro-benzo[b][1,4]diazepin-2-one,
4-[3-(2-hydroxymethyl-pyridin-4-yl)-phenyl]-7-methyl-8-trifluoromethyl-1,3-dihydro benzo[b][1,4]diazepin-2-one,
4-[2,3']bipyridinyl-4-yl-7-methyl-8-trifluoromethyl-1,3-dihydro-benzo[b][1,4]diazepin-2-one,
7-methyl-4-(2'-methyl-[2,4']bipyridinyl-4-yl)-8-trifluoromethyl-1,3-dihydro-benzo-[b][1,4]diazepin-2-one, and
4-[3-(6-methyl-pyrimidin-4-yl)-phenyl]-8-trifluoromethyl-1,3-dihydro-benzo[b][1,4]diazepin-2-one.

\* \* \* \* \*